United States Patent
Tange et al.

(10) Patent No.: US 9,511,211 B2
(45) Date of Patent: Dec. 6, 2016

(54) MEDICAL SYSTEM INCLUDING A PLURALITY OF CAPSULE TYPE MEDICAL DEVICES

(71) Applicant: Sony Corporation, Tokyo (JP)

(72) Inventors: Akira Tange, Tokyo (JP); Yoichiro Sako, Tokyo (JP); Takatoshi Nakamura, Kanagawa (JP); Yuki Koga, Tokyo (JP); Katsumi Ando, Tokyo (JP)

(73) Assignee: SONY CORPORATION, Tokyo (JP)

( * ) Notice: Subject to any disclaimer, the term of this patent is extended or adjusted under 35 U.S.C. 154(b) by 158 days.

(21) Appl. No.: 14/384,865

(22) PCT Filed: Jan. 17, 2013

(86) PCT No.: PCT/JP2013/050781
§ 371 (c)(1),
(2) Date: Sep. 12, 2014

(87) PCT Pub. No.: WO2013/145814
PCT Pub. Date: Oct. 3, 2013

(65) Prior Publication Data
US 2015/0045658 A1 Feb. 12, 2015

(30) Foreign Application Priority Data

Mar. 27, 2012 (JP) ................ 2012-071828

(51) Int. Cl.
*A61M 31/00* (2006.01)
*A61B 1/00* (2006.01)
(Continued)

(52) U.S. Cl.
CPC .......... *A61M 31/00* (2013.01); *A61B 1/00006* (2013.01); *A61B 1/041* (2013.01); *A61B 1/06* (2013.01); *A61B 5/0084* (2013.01); *A61B 5/065* (2013.01); *A61B 5/073* (2013.01); *A61B 5/4839* (2013.01); *A61B 10/04* (2013.01); *A61M 5/172* (2013.01); *A61M 37/00* (2013.01); *A61B 1/00082* (2013.01); *A61B 1/053* (2013.01);
(Continued)

(58) Field of Classification Search
CPC ... A61B 10/04; A61B 1/0006; A61B 1/00082; A61B 1/041; A61B 1/053; A61B 1/06; A61B 2562/162; A61B 5/0031; A61B 5/0084; A61B 5/065; A61B 5/073; A61B 5/4839; A61M 2205/33; A61M 2205/3306; A61M 2205/3584; A61M 2205/50; A61M 31/00; A61M 31/002; A61M 37/00; A61M 5/172
See application file for complete search history.

(56) References Cited

U.S. PATENT DOCUMENTS

| 2003/0018280 A1 | 1/2003 | Lewkowicz et al. |
| 2005/0043587 A1 | 2/2005 | Fujimori et al. |

(Continued)

FOREIGN PATENT DOCUMENTS

| JP | 2003-325438 A | 11/2003 |
| JP | 2004-329292 A | 11/2004 |

(Continued)

*Primary Examiner* — Ruth S Smith
(74) *Attorney, Agent, or Firm* — Chip Law Group

(57) ABSTRACT

Provided is a medical system including a first capsule type medical device, and a second capsule type medical device. The first and second capsule type medical devices operate in cooperation with each other in a body.

8 Claims, 17 Drawing Sheets

(51) Int. Cl.

| | |
|---|---|
| *A61B 1/04* | (2006.01) |
| *A61B 5/07* | (2006.01) |
| *A61B 1/06* | (2006.01) |
| *A61B 10/04* | (2006.01) |
| *A61M 5/172* | (2006.01) |
| *A61M 37/00* | (2006.01) |
| *A61B 5/06* | (2006.01) |
| *A61B 1/05* | (2006.01) |
| *A61B 5/00* | (2006.01) |

(52) U.S. Cl.
CPC ....... *A61B 5/0031* (2013.01); *A61B 2562/162* (2013.01); *A61M 31/002* (2013.01); *A61M 2205/33* (2013.01); *A61M 2205/3306* (2013.01); *A61M 2205/3538* (2013.01); *A61M 2205/3584* (2013.01); *A61M 2205/50* (2013.01)

(56) References Cited

U.S. PATENT DOCUMENTS

| | | |
|---|---|---|
| 2005/0148847 A1 | 7/2005 | Uchiyama et al. |
| 2005/0158246 A1 | 7/2005 | Takizawa et al. |
| 2008/0199065 A1 | 8/2008 | Swain |
| 2008/0312532 A1 | 12/2008 | Van Pieterson et al. |

FOREIGN PATENT DOCUMENTS

| | | |
|---|---|---|
| JP | 2005-052358 A | 3/2005 |
| JP | 2005-102851 A | 4/2005 |
| JP | 2005-103130 A | 4/2005 |
| JP | 2005-334331 A | 12/2005 |
| JP | 2006-149689 A | 6/2006 |
| JP | 2007-537817 A | 12/2007 |
| JP | 2009-515633 A | 4/2009 |
| JP | 2010-005129 A | 1/2010 |
| JP | 2010-005442 A | 1/2010 |

FIG. 10
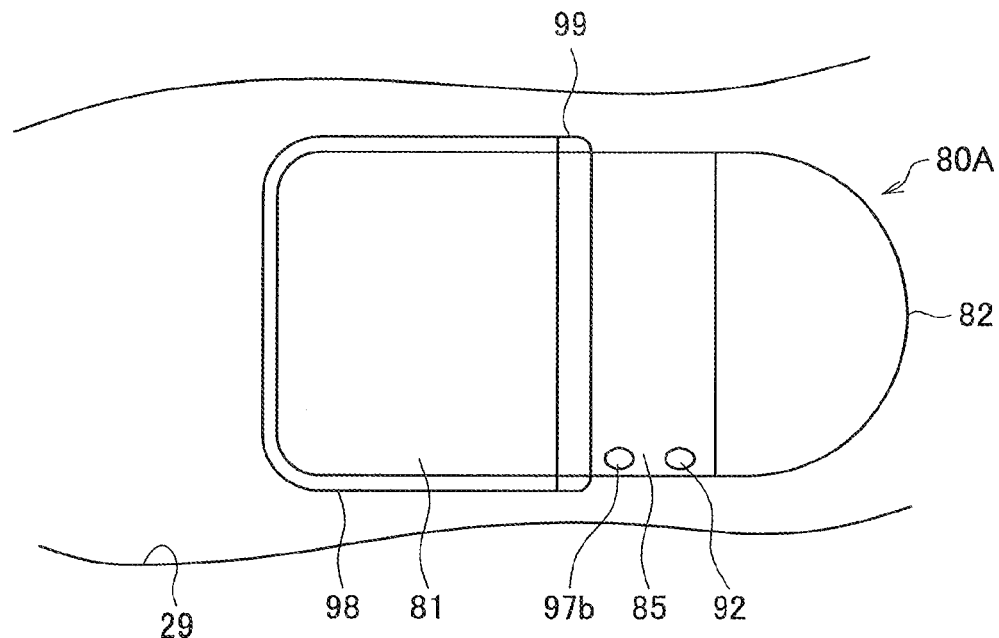
IN MOVEMENT
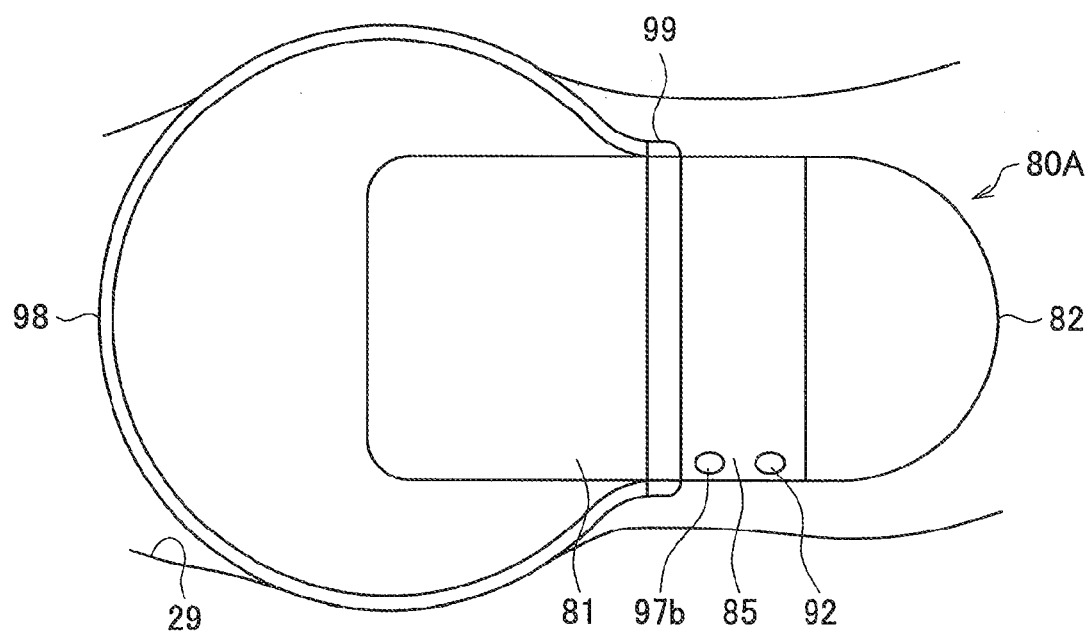
SUSPENSION MEANS OPERATED

FIG. 17

COOPERATION BETWEEN PHOTOGRAPHING AND LIGHTING (STEP S280)

| | | CAPSULE 200A | | CAPSULE 200B | |
|---|---|---|---|---|---|
| | | LIGHTING UNIT 203A | LIGHTING UNIT 204A | LIGHTING UNIT 203B | LIGHTING UNIT 204B |
| CAPSULE 200A | PHOTOGRAPHING UNIT 205A | | | O | — |
| | PHOTOGRAPHING UNIT 206A | | | — | O |
| CAPSULE 200B | PHOTOGRAPHING UNIT 205B | O | — | | |
| | PHOTOGRAPHING UNIT 206B | — | O | | |
| | PHOTOGRAPHING UNIT 205B | O | — | | |
| | PHOTOGRAPHING UNIT 206B | — | O | | |

MEDICAL SYSTEM INCLUDING A PLURALITY OF CAPSULE TYPE MEDICAL DEVICES

TECHNICAL FIELD

The present disclosure relates to a medical system.

BACKGROUND ART

In recent years, a capsule type medical device to be introduced into a body of a test object is known. Such a known medical device photographs sites in the body at random, extracts a sample or the like from the body, or discharge a medicine, for example.

In particular, as for a capsule type medical device discharging a medicine, there is proposed a device that discharges a medicine at a desired position (a desired affected part) among sites in the body.

For example, the following Patent Literature 1 proposes a capsule type medical device which is caused to spray a medicine by application of a rotating magnetic field from an external rotating magnetic field generating device when the capsule type medical device moves to the desired site in the body of the test object.

Further, the following Patent Literature 2 proposes a capsule type medical device which discharges a medicine when the capsule type medical device receives a discharge signal from an extracorporeal device which determines whether the capsule has reached the position of an affected part and transmits the discharge signal to the capsule in a case where the capsule has reached the position of the affected part.

CITATION LIST

Patent Literature

Patent Literature 1: JP 2003-325438A
Patent Literature 2: JP 2005-334331A

SUMMARY OF INVENTION

Technical Problem

However, any of medical devices described above has a single capsule type medical device to be introduced into the body of the test object, and does not have a function of performing treatment by use of a plurality of medical devices in cooperation with each other.

Accordingly, the present disclosure proposes a medical system that performs more effective treatment by cooperative operation of a plurality of capsule type medical devices.

Solution to Problem

According to the present disclosure, there is proposed a medical system including a first capsule type medical device, and a second capsule type medical device. The first and second capsule type medical devices operate in cooperation with each other in a body.

Advantageous Effects of Invention

As described above, according to the present disclosure, it becomes possible to perform more effective treatment by cooperative operation of a plurality of capsule type medical devices.

BRIEF DESCRIPTION OF DRAWINGS

FIG. 10 is an outline drawing of a capsule type medical device according to a second embodiment.
FIG. 17 is a table showing combination of photographing and lighting according to a third embodiment.

DESCRIPTION OF EMBODIMENTS

Hereinafter, preferred embodiments of the present invention will be described in detail with reference to the appended drawings. Note that, in this specification and the drawings, elements that have substantially the same function and structure are denoted with the same reference signs, and repeated explanation is omitted.

<1. Overview of Medical System According to Embodiment of Present Disclosure>

Figure 1:
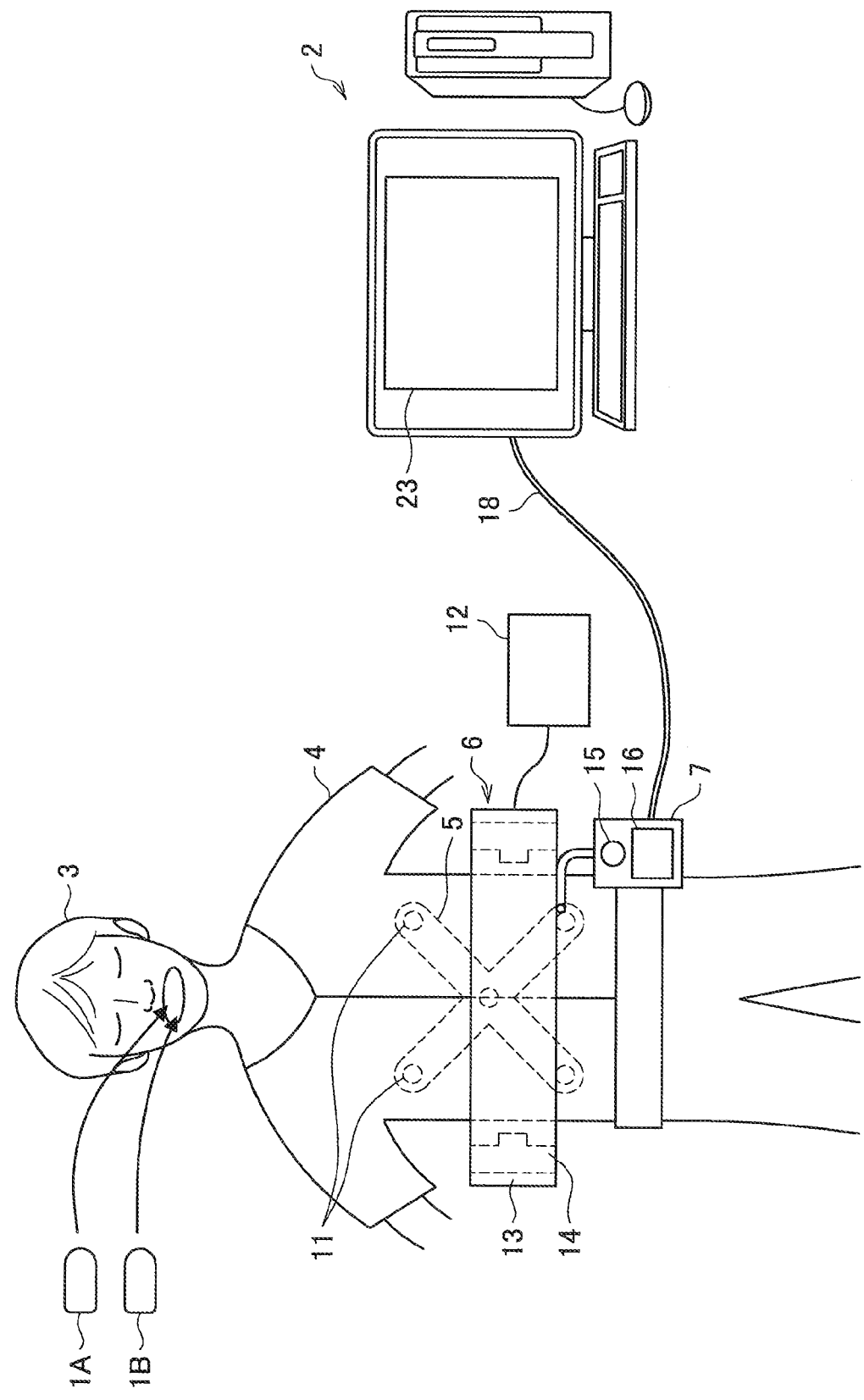
FIG. 1 is a view showing an overview of a medical system according to an embodiment of the present disclosure.

First, an overview of a medical system according to an embodiment of the present disclosure will be described with reference to FIG. 1. As shown in FIG. 1, the medical system according to an embodiment of the present disclosure includes capsule type medical devices 1A and 1B (hereinafter also referred to as capsules 1A and 1B), a rotating magnetic field generating device 6, and a control device 2. Note that the capsules 1A and 1B have the same configuration, and accordingly, in a case where individual capsules do not need to be described separately, the capsules are referred to as capsule 1.

The capsule 1 is swallowed through the mouth of a test object 3, as shown in FIG. 1, and transmits an image signal (a photographed image) obtained when the capsule 1 photographs an inner wall of an intracelom pipeline optically when passing through the intracelom pipeline.

As shown in FIG. 1, further, the test object 3 wears a shield shirt 4. The shield shirt 4 has a shielding function, and includes an antenna unit 5 attached inside, the antenna unit 5 having a plurality of antennas 11. The antenna unit 5 outputs, to an extracorporeal unit 7 connected to the antenna unit 5, the received photographed image that is transmitted from the capsule 1 and received by the antennas 11.

The extracorporeal unit 7 is attached to a belt of the test object 3 with a detachable hook, for example, and retains the photographed image that is outputted from the antenna unit 5. Further, the extracorporeal unit 7 has a box shape as shown in FIG. 1, for example, and includes an operation button 15 for performing control operation and a liquid crystal monitor 16 for displaying an image, the operation button 15 and the liquid crystal monitor 16 being provided on a front surface of the extracorporeal unit 7.

The photographed image retained in the extracorporeal unit 7 may be displayed on the liquid crystal monitor 16 during or after testing, or may be transmitted to the control device 2 during or after testing so as to be displayed on a display unit 23 of the control device 2. The extracorporeal unit 7 and the control device 2 may be detachably connected to each other with a wire, for example, via a communication cable such as an USB cable 18, as shown in FIG. 1, or may be wirelessly connected to each other.

Accordingly, during or after testing, a medical staff can check the photographed image of the inside of the intracelom pipeline of the test object 3 with the liquid crystal monitor 16 of the extracorporeal unit 7 or the display unit 23 of the control device 2.

Further, as shown in FIG. 1, the rotating magnetic field generating device 6 is disposed on the periphery of the test object 3, such as a waist part of the test object 3. In the rotating magnetic field generating device 6, electromagnets 14 are arranged at a plurality of portions in the circumferential direction of a ring-shape frame member 13 and magnetic poles of the electromagnets 14 repel each other. The rotating magnetic field generating device 6 includes a driver circuit 12 which supplies driving signals to the electromagnets 14.

The capsule 1 according to the present embodiment has a structure such that a medicine is stored therein and allows the medicine to be discharged by generation of a rotating magnetic field. The rotating magnetic field is generated by the operation of the above described driver circuit 12 and sequential supply of direct current, as driving signals, from the driver circuit 12 to the electromagnets 14 at a plurality of portions.

Operation timing of the driver circuit 12 may be based on operation on a switch (not shown) of the driver circuit 12, the operation being made by a medical staff who has checked an affected part with the photographed image displayed on the liquid crystal monitor 16 of the extracorporeal unit 7 or the display unit 23 of the control device 2, for example. Alternatively, the driver circuit 12 may operate in accordance with an operation signal from the control device 2.

Here, in a case where a single capsule is introduced into the body, it has been difficult to allow a plurality of capsules to cooperate with each other to discharge the medicine in the body, or to photograph.

Accordingly, according to an embodiment of the present disclosure, there is provided a medical system that can perform more effective treatment by cooperative operation of a plurality of capsule type medical devices.

The overview of the medical system according to an embodiment of the present disclosure has been described above. Next, a plurality of embodiments of the medical system according to the present disclosure will be specifically described.

<2. Embodiments>
(2-1. First Embodiment)

As shown in FIG. 1, a medical system according to a first embodiment includes the capsules 1A and 1B, which are to be introduced into the body of the test object 3, and the control device 2. A basic configuration of the control device 2, a structure of the capsule 1, and cooperative operation according to the first embodiment will be described in sequence below.

(2-1-1. Configuration of Control Device)

Figure 2:
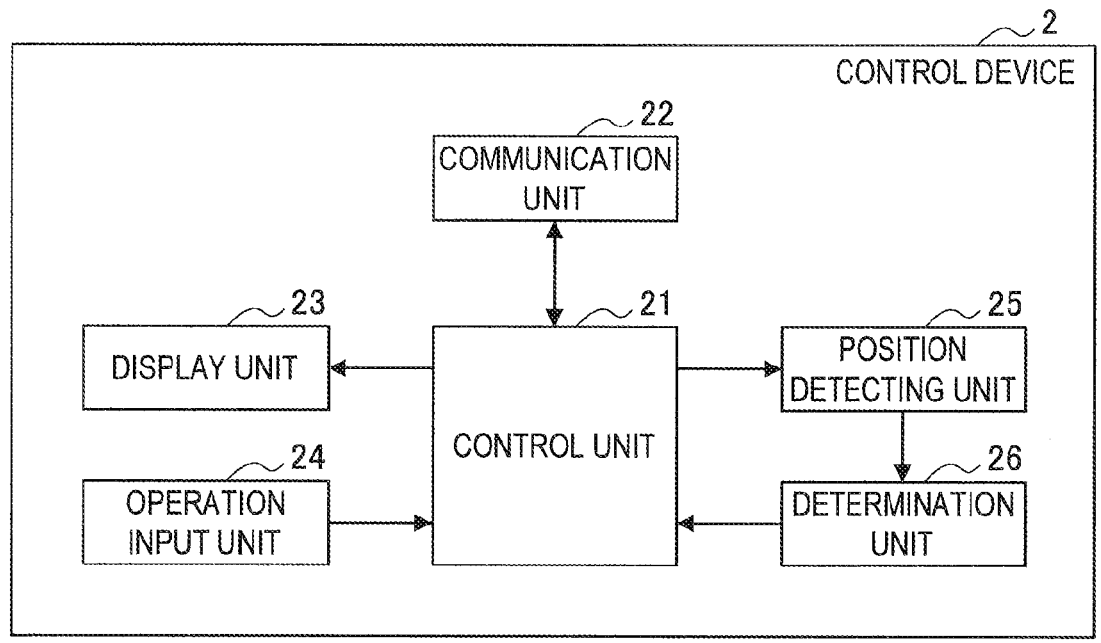
FIG. 2 is a block diagram showing a configuration of a control device according to a first embodiment.

FIG. 2 is a block diagram showing the configuration of the control device 2 according to the first embodiment. As shown in FIG. 2, the control device 2 includes a control unit 21, a communication unit 22, the display unit 23, an operation input unit 24, a position detecting unit 25, and a determination unit 26.

The communication unit 22 is connected to an external device and has a function of transmitting and receiving data. For example, the communication unit 22 is connected to the extracorporeal unit 7 and receives the photographed image and signals for position detection from the capsule 1 via the extracorporeal unit 7. Further, the communication unit 22 may be connected to the rotating magnetic field generating device 6 with or without wires so as to transmit an operation signal for operating the driver circuit 12.

The display unit 23 has a function of displaying a screen including images and texts under control of the control unit 21. Further, the display unit 23 is achieved by a liquid crystal display (LCD), an organic light-emitting diode (OLED), a cathode ray tube (CRT), or the like.

More specifically, the display unit 23 displays the photographed image received from the capsule 1 via the extracorporeal unit 7, for example. Thus, a medical staff can check the photographed image of the inside of the body of the test object 3 to recognize the position of the capsule 1 or determine whether or not the capsule 1 is located at a specific site where the medicine is to be discharged. Further, the display unit 23 may display a screen for specification for accepting registration of the specific site where a predetermined medicine is to be discharged. The specification of a medicine sprayed site by use of the screen for specification will be described later in detail in "2-2-4. Specification of medicine sprayed site."

The operation input unit 24 has functions of detecting operation made by the medical staff and of outputting an input signal generated on the basis of the detected operation input to the control unit 21. The operation input unit 24 is achieved by a mouse, a keyboard, a touch panel, and the like. The medical staff can operate the operation input unit 24 to perform operation such as the registration of the specific site.

The control unit 21 has a function of controlling the whole control device 2. For example, the control unit 21 performs control such that the photographed image received by the communication unit 22 is displayed on the display unit 23.

The control unit 21 according to the present embodiment may control the communication unit 22 on the basis of determination results that are outputted from the determination unit 26 and may transmit an operation signal to the rotating magnetic field generating device 6. More specifically, in a case where the determination unit 26 determines that the capsule 1 has reached the medicine sprayed site or the vicinity of the medicine sprayed site which is specified in advance, the control unit 21 controls the communication unit 22 and transmits the operation signal to the rotating magnetic field generating device 6.

The position detecting unit 25 detects (calculates) the position of the capsule 1 on the basis of the signal for position detection, which is received by the communication unit 22 from the capsule 1. Here, the signal for position detection may be position information or the photographed image. The position detecting unit 25 may analyze the photographed image of the inside of the body, photographed by the capsule 1, to detect the position of the capsule 1. Further, the position detecting unit 25 outputs the detected position of the capsule 1 to the determination unit 26.

The determination unit 26 determines whether or not the position of the capsule 1, which is detected by the position detecting unit 25, is at the medicine sprayed site or in the vicinity of the medicine sprayed site which is specified in advance, and outputs the determination results to the control unit 21. Note that, as described above, the specific site where the medicine is to be sprayed in the body may be registered in advance by the medical staff.

The configuration of the control device 2 according to the first embodiment has been described above in detail. Next, the structure of the capsule 1 according to the first embodiment will be described with reference to FIG. 3 to FIG. 5.

(2-1-2. Structure of Capsule Type Medical Device)

Figure 3:
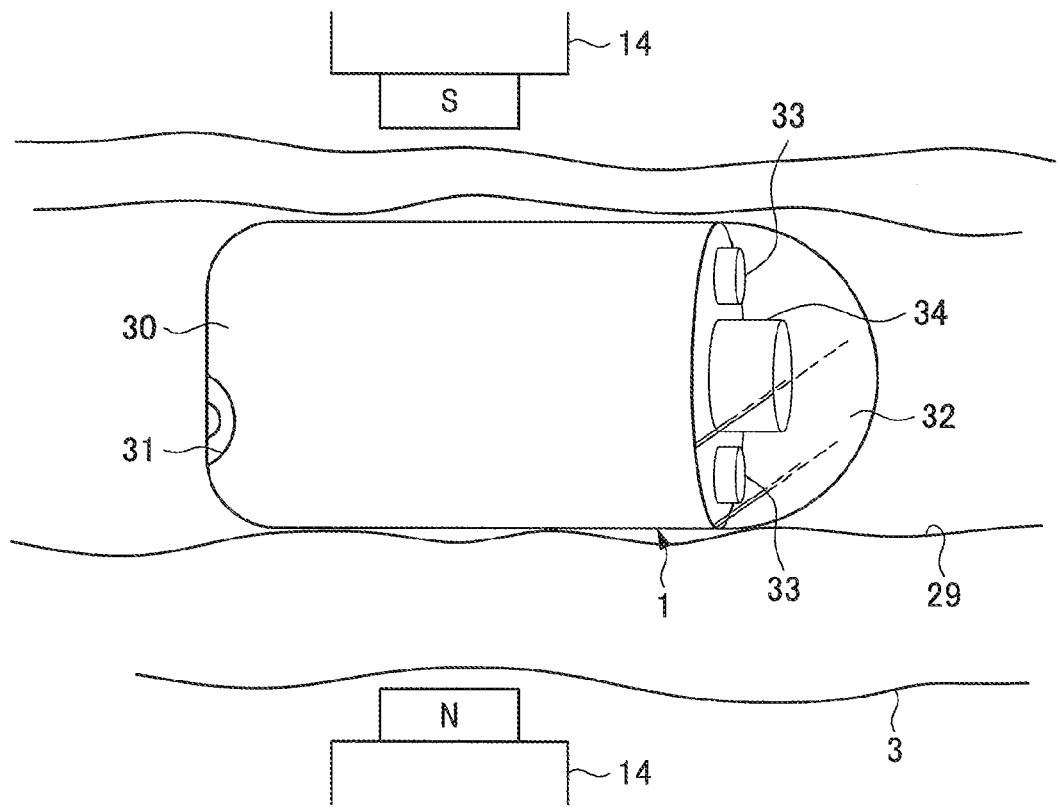
FIG. 3 is an outline drawing of a capsule type medical device according to a first embodiment.

FIG. 3 is an outline drawing of the capsule 1 according to the first embodiment. As shown in FIG. 3, the capsule 1 to be inserted into an intracelom pipeline 29 of the test object 3 has a substantially cylindrical shape, and is covered with an outer case 30 having by a curved rear end of the capsule 1. Further, a rear end portion of the outer case 30 is provided with an opening 31 through which the medicine is to be discharged, and a hemispherical transparent cover 32 is watertightly connected and secured to a tip portion of the outer case 30.

Inside a container that is sealed hermetically inside the transparent cover 32, as shown in FIG. 3, a photographing optical system 34 is disposed at the center facing the transparent cover 32, and lighting units such as white LEDs 33 are disposed on the periphery of the photographing optical system 34.

In a case where the capsule 1 reaches the predetermined site or the vicinity of the predetermined site in the body, driving current is supplied to the plurality of electromagnets 14 of the rotating magnetic field generating device 6, which are arranged on the periphery of the site, so that a rotating magnetic field is generated and the medicine is discharged through the opening 31 of the capsule 1.

More specifically, a moving body 52 provided inside the capsule 1 to be rotatable is caused to move by the rotating magnetic field, so that a state in which an opening in a storage unit inside the capsule 1 is closed becomes a state in which the storage unit communicates with the outside, and thereby the medicine stored in the storage unit is discharged.

Such an internal structure of the capsule 1 will be specifically described below with reference to FIG. 4 and FIG. 5. Note that FIG. 4 and FIG. 5 show the capsule 1A storing a medicine A as an example; however, the capsule 1B storing a medicine B has the same structure.

Figure 4:
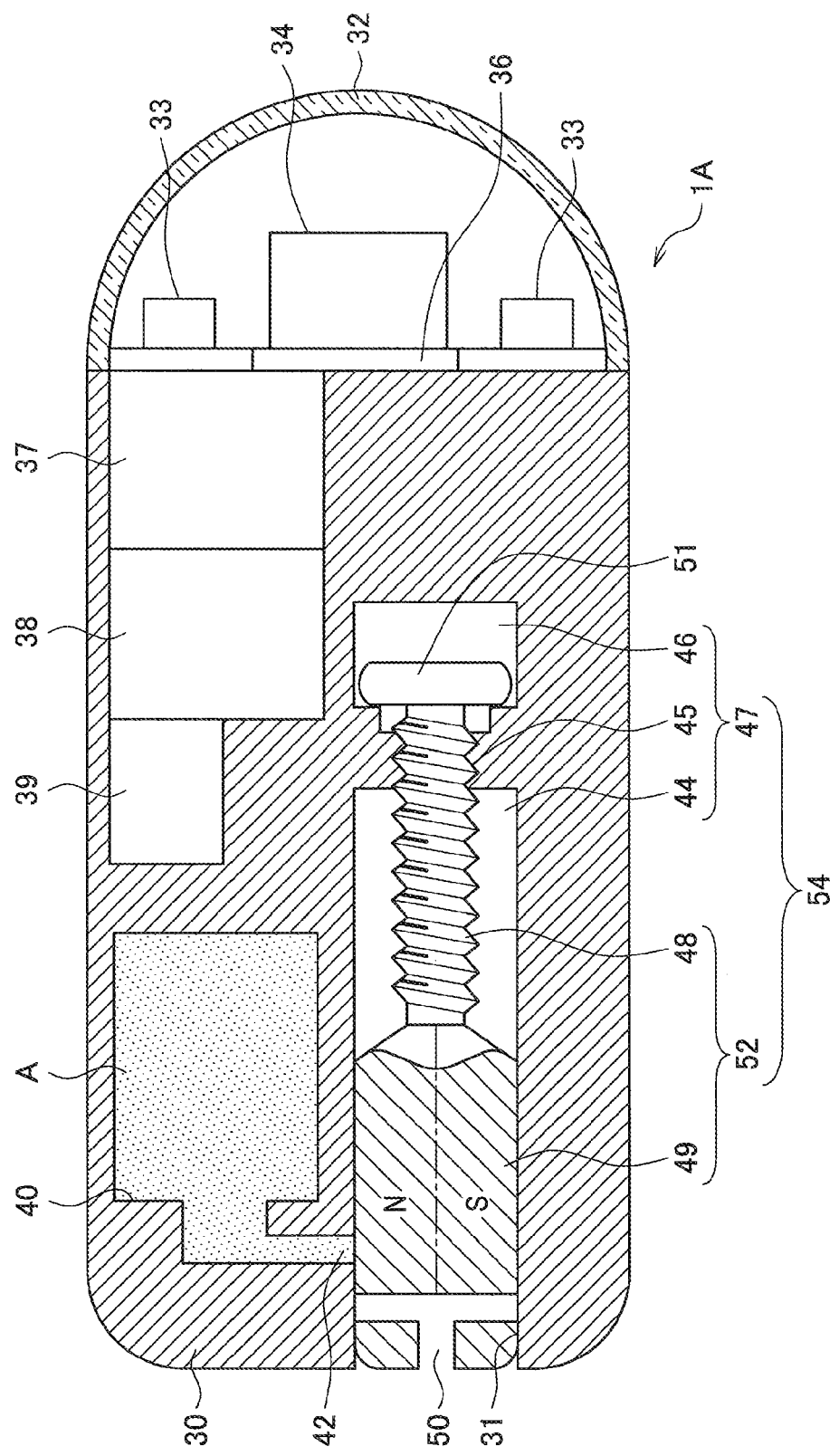
FIG. 4 shows an internal structure in a state where a moving body in a capsule type medical device according to a first embodiment closes an opening in a storage unit.
Figure 5:
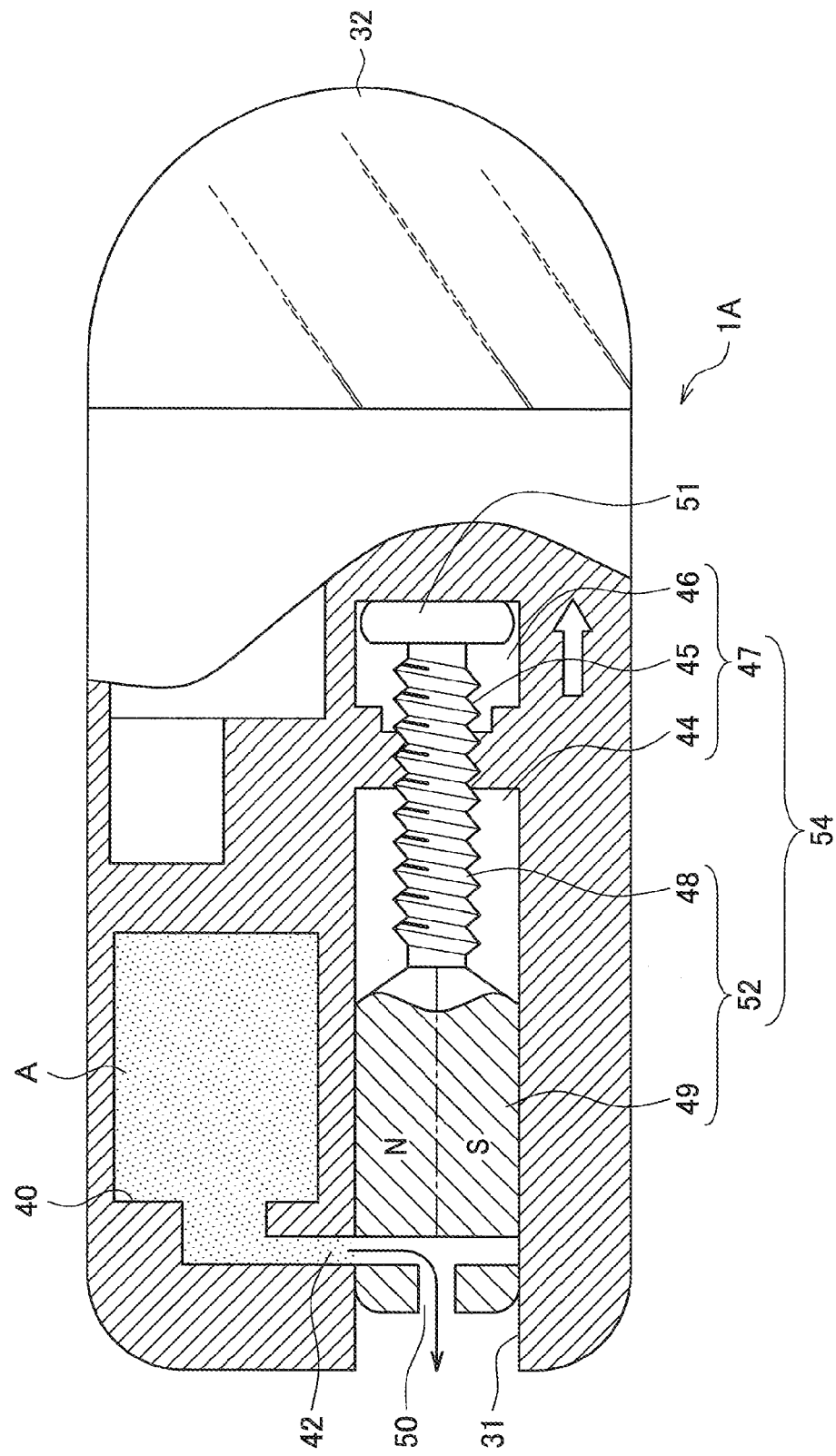
FIG. 5 shows an internal structure in a state where the storage unit is made to communicate with the outside by movement of a moving body in a capsule type medical device according to a first embodiment.

FIG. 4 shows an internal structure in a state where the moving body in the capsule 1A closes an opening in the storage unit. FIG. 5 shows an internal structure of a main unit of the capsule 1A in a state where the storage unit is made to communicate with the outside by rotatable movement of the moving body.

As shown in FIG. 4, at a position where an image is formed in the photographing optical system 34 disposed in the center portion facing the transparent cover 32, a photographing sensor 36 such as a CMOS imager (or a CCD) is disposed.

In a backward upper portion of the photographing sensor 36, a control unit 37, a memory and communication unit 38, and a battery 39 are disposed. The control unit 37 drives the photographing sensor 36, performs signal processing of an output signal of the photographing sensor 36, and controls other circuits such as the memory and communication unit 38 which will be described next.

The memory and communication unit 38 has a function of memorizing the photographed image signal (the photographed image) and a communication function of transmitting the image signal wirelessly, for example.

The battery 39 has a button shape, for example, is in conduction with a wiring substrate that is not shown, and supplies power by electrically connecting to each structural element of the capsule 1A via the wiring substrate.

As shown in FIG. 4, a storage unit 40 is provided in a portion that is shielded from the battery 39, the memory and communication unit 38, and the control unit 37 by a wall portion due to the outer case 30, the portion being located at the backward (left) of the battery 39.

The medicine A to be stored in the storage unit 40 is inserted in advance, in addition to a pressurized gas, through a horizontal hole that is not shown. The horizontal hole is closed with a rubber stopper or the like after the medicine is inserted.

As shown in FIG. 4, the storage unit 40 is provided eccentrically in the upward direction from the center axis of the capsule 1A. Meanwhile, a medicine discharging unit 54, which discharges the medicine A from the storage unit 40, is provided eccentrically in the downward direction from the center axis of the capsule 1A on the side opposite to the storage unit 40.

The medicine discharging unit 54 according to the first embodiment, as shown in FIG. 4, is achieved by the moving body 52 and a moving body storing unit 47 which disposes or supports the moving body 52 such that the moving body 52 can rotatably move in the longitudinal direction of the capsule 1A.

The moving body storing unit 47 includes a first depressed portion 44 having the opening 31 as a rear end, a screw hole (a female screw) 45 formed on a front end side of the first depressed portion 44, and a second depressed portion 46 which communicates with the first depressed portion 44 through the screw hole 45. Note that on a side portion of the first depressed portion 44, an opening 42 of a pipeline that communicates with the storage unit 40 is open.

The moving body storing unit 47 stores and supports the moving body 52 in a state where a screw portion (a male screw portion) 48 provided on the front end side of the moving body 52 is screwed into the screw hole 45.

The moving body 52 is provided with the screw portion 48 on the front end side, as described above, and at the tip of the screw portion 48 (the front end of the moving body 52), for example, a disk-shape stopper 51 is further provided. The stopper 51 is stored inside the second depressed portion 46. Further, on the rear end side of the moving body 52, a cylindrical portion 49 which fits the first depressed portion 44 is provided, and in the vicinity of the rear end of the cylindrical portion 49, for example, a T-shape hole 50 is provided.

In the state shown in FIG. 4, the moving body 52 closes the opening 42 with the cylindrical portion 49. Here, the moving body 52 is formed of a permanent magnet in which both sides of the center axis shown by a dashed line (e.g., the upper part and the lower part of the center axis) are magnetized with N and S, for example. Accordingly, in the state shown in FIG. 4, the generation of the rotating magnetic field by the electromagnets 14 shown in FIG. 3 causes the moving body 52 to rotate and to move to a tip direction (the right direction), as shown in FIG. 5.

In the state shown in FIG. 5, the moving body 52 rotates, and moves to the tip direction (the right direction) to the position where the stopper 51 touches a wall surface of the second depressed portion 46, for example. In this case, the T-shape hole 50 of the moving body 52 communicates with the opening 42, and the medicine A stored in the storage unit 40 is discharged to the outside of the capsule 1A through the opening 42 and the T-shape hole 50.

As described above with reference to FIG. 4 and FIG. 5, in the present embodiment, the moving body 52 included in the medicine discharging unit 54 inside the capsule 1A rotates and moves in accordance with the generation of the external rotating magnetic field, so that the opening 42 which communicates with the storage unit 40 storing the medicine A is open and closed. Note that, as described above, the internal structure of the capsule 1B is the same as that of the capsule 1A shown in FIG. 4 and FIG. 5, and therefore, an individual description is omitted.

Next, cooperative operation of the plurality of capsules 1A and 1B having the above described structure will be specifically described with reference to FIG. 6. In the present embodiment, cooperative operation of mix-spraying of a medicine will be described as an example.

(2-1-3. Cooperative Operation)

Figure 6:
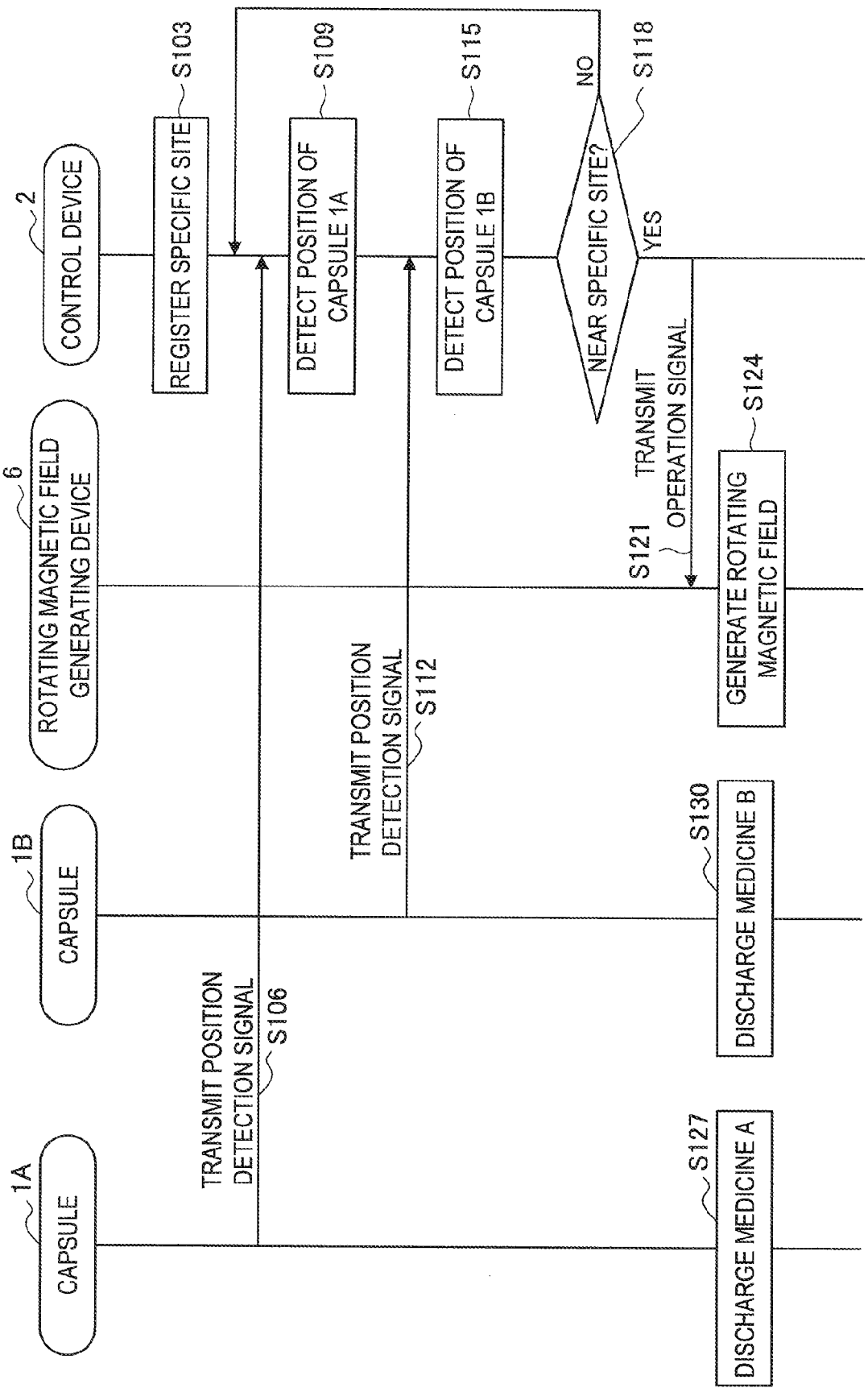
FIG. 6 is a flowchart showing cooperative operation according to a first embodiment.

FIG. 6 is a flowchart showing cooperative operation according to the first embodiment. As shown in FIG. 6, first, in step S103, the control device 2 registers the specific site where the medicine is to be sprayed (discharged). More specifically, the control device 2 memorizes the specific site where the medicine is to be sprayed in association with the medicine to be sprayed at the specific site on the basis of an operation input made by the medical staff, for example.

Next, in step S106, the power is applied to the capsule 1A, and the capsule 1A swallowed by the test object 3 transmits a position detection signal.

Next, in step S109, the position detecting unit 25 of the control device 2 detects the position of the capsule 1A on the basis of the intensity of the position detection signal transmitted from the capsule 1A. Note that in a case where the photographed image is transmitted as the position detection signal from the capsule 1A, the position detecting unit 25 may detect the position of the capsule 1A by analyzing the photographed image.

Meanwhile, in step S112, the power is applied to the capsule 1B, and the capsule 1B swallowed by the test object 3 at substantially the same time as the capsule 1A also transmits a position detection signal.

Next, in step S115, the position detecting unit 25 of the control device 2 detects the position of the capsule 1B on the basis of the intensity of the position detection signal transmitted from the capsule 1B. Note that in a case where the photographed image is transmitted as the position detection signal from the capsule 1B, the position detecting unit 25 may detect the position of the capsule 1B by analyzing the photographed image.

Next, in step S118, the determination unit 26 of the control device 2 determines whether or not the positions of the capsules 1A and 1B detected by the position detecting units 25 are the specific site or the vicinity of the specific site which is registered in the step S103. For example, the determination unit 26 determines that the capsule 1 has reached the specific site or the vicinity of specific site in a case where the capsules 1A and 1B are within a predetermined distance from the specific site registered in advance.

Next, in a case where the determination unit 26 determines that the capsules 1A and 1B have reached the specific site or the vicinity of the specific site, in step S121, the control device 2 performs control such that an operation signal is transmitted to the rotating magnetic field generating device 6 so that the capsules 1A and 1B can discharge the medicine at substantially the same time.

Next, in step S124, the rotating magnetic field generating device 6 causes the driver circuit 12 to operate in accordance with the operation signal, and sequentially supplies direct current as driving signals to the electromagnets 14 at a plurality of portions from the driver circuit 12, so that the rotating magnetic field is generated.

Next, in step S127, the capsule 1A discharges the medicine A. As described above, when the rotating magnetic field is applied, the moving body 52 of the capsule 1A rotates and moves, and as shown in FIG. 5, the opening 42 of the storage unit 40 storing the medicine A communicates with the outside through the T-shape hole 50 of the moving body 52. Accordingly, the medicine A of the storage unit 40 is discharged to the outside of the capsule 1A and the medicine A is sprayed to the specific site and the vicinity of the specific site.

Further, in step S130, the capsule 1B discharges the medicine B. As described above, since the internal structure of the capsule 1B is the same as that of the capsule 1A, when the rotating magnetic field is applied, the moving body 52 inside the capsule 1B rotates and moves, and the opening 42 of the storage unit 40 storing the medicine B communicates with the outside through the T-shape hole 50 of the moving body 52. Accordingly, the medicine B of the storage unit 40 is discharged to the outside of the capsule 1B and the medicine B is sprayed to the specific site and the vicinity of the specific site.

As described above, by cooperative operation of the capsule 1 according to the first embodiment, the plurality of medicines A and B can be mixed and sprayed to the specific site.

(2-1-4. Specification of Medicine Sprayed Site)

Next, registration of the specific site shown in the step S103 in FIG. 6 will be described. The medical staff can register intuitively the specific site where each medicine is to be sprayed in accordance with a specification screen displayed on the display unit 23 of the control device 2. An example of the specification screen will be specifically described below with reference FIG. 7 and FIG. 8.

Figure 7:
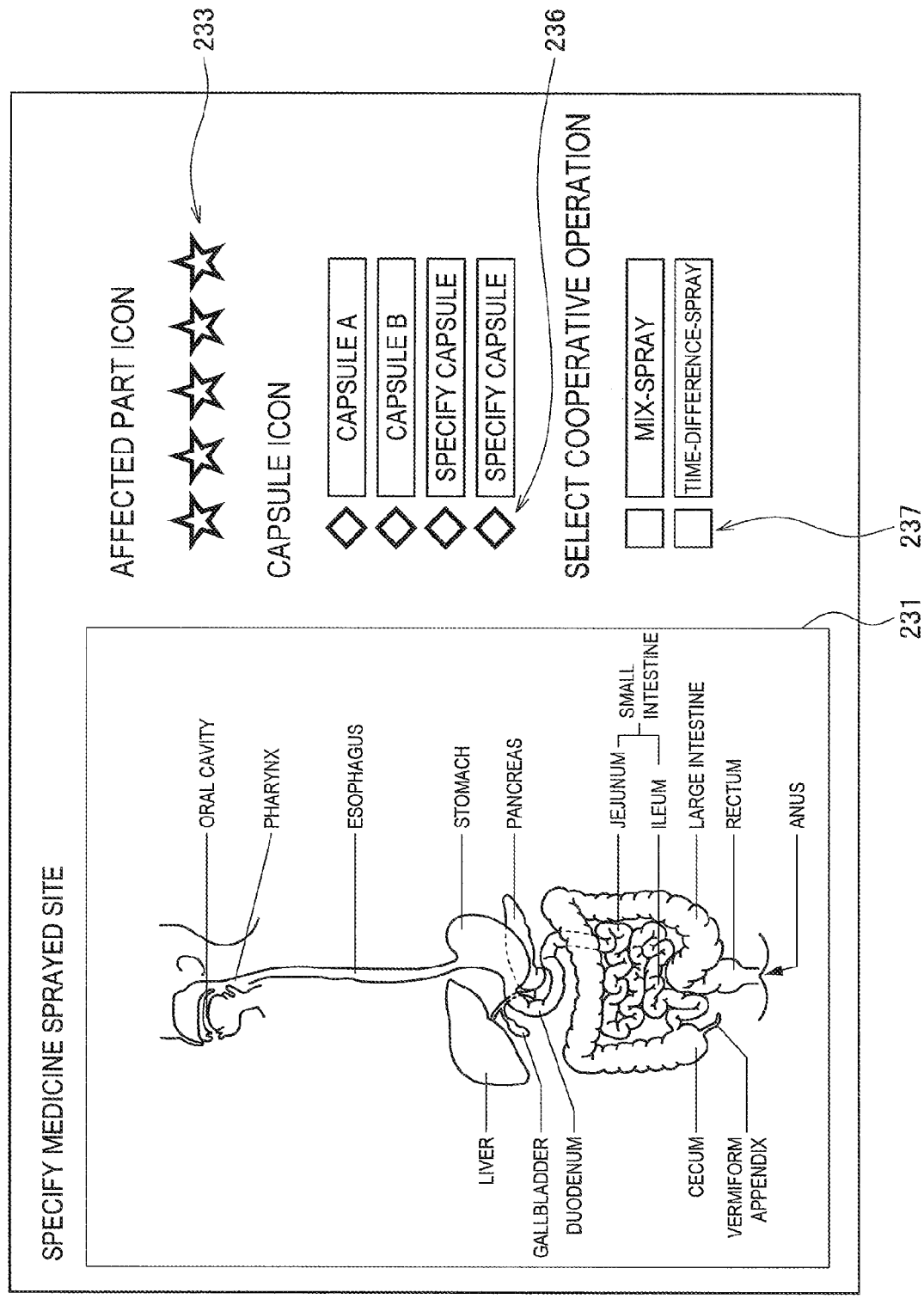
FIG. 7 shows an example of a specification screen according to a first embodiment.

FIG. 7 shows an example of a medicine sprayed site specification screen which is displayed on the display unit 23 of the control device 2 according to the first embodiment. As shown in FIG. 7, the medicine sprayed site specification screen includes a site image 231 representing sites in the body, an affected part icon 233, a capsule icon 236, and a checkbox 237 for selecting cooperative operation.

The site image 231 may be an image in which an illustration of each site is in association with the name thereof, as shown in FIG. 7. Note that the example shown in FIG. 7 shows a standard illustration of sites of the body as the site image 231; however, an actual position of the body of the test object 3 is substantially fixed, and the absolute position (the position coordinate) of each internal organ (each site) has been recognized already by the control unit 21 of the control device 2. Accordingly, the control unit 21 can calculate the position coordinate of the site of the test object 3, which corresponds to each site represented in the site image 231.

The affected part icon 233 is an icon for specifying the site to which the medicine is to be sprayed. Further, the capsule icon 236 is an icon for specifying the capsule that is to spray the medicine.

The checkbox 237 for selecting cooperative operation is a checkbox for selecting what kind of cooperative operation the plurality of capsule type medical devices to be introduced into the test object 3 perform. Examples of cooperative operation that can be selected include "mix-spraying" in which the plurality of capsules 1 discharge the medicine to the specific site at substantially the same time, and "time-difference-spraying". The "time-difference-spraying" is cooperative operation in which, after a predetermined time passes after one of the capsules discharges the medicine to the specific site or the vicinity of the specific site, the other capsule discharges the medicine to the specific site or the vicinity of the specific site.

Although not included in the choices of cooperative operation shown in FIG. 7, other examples can be included in cooperative operation according to the present disclosure. For example, the plurality of capsules may cooperatively play different roles (e.g., lighting and photographing, marking and photographing, marking and discharging the medicine, or marking and extraction), or such cooperative operation that the following capsule operates in accordance with the results of treatment by the precedent capsule. Note that specific contents of such other cooperative operation will be described later.

Figure 8:
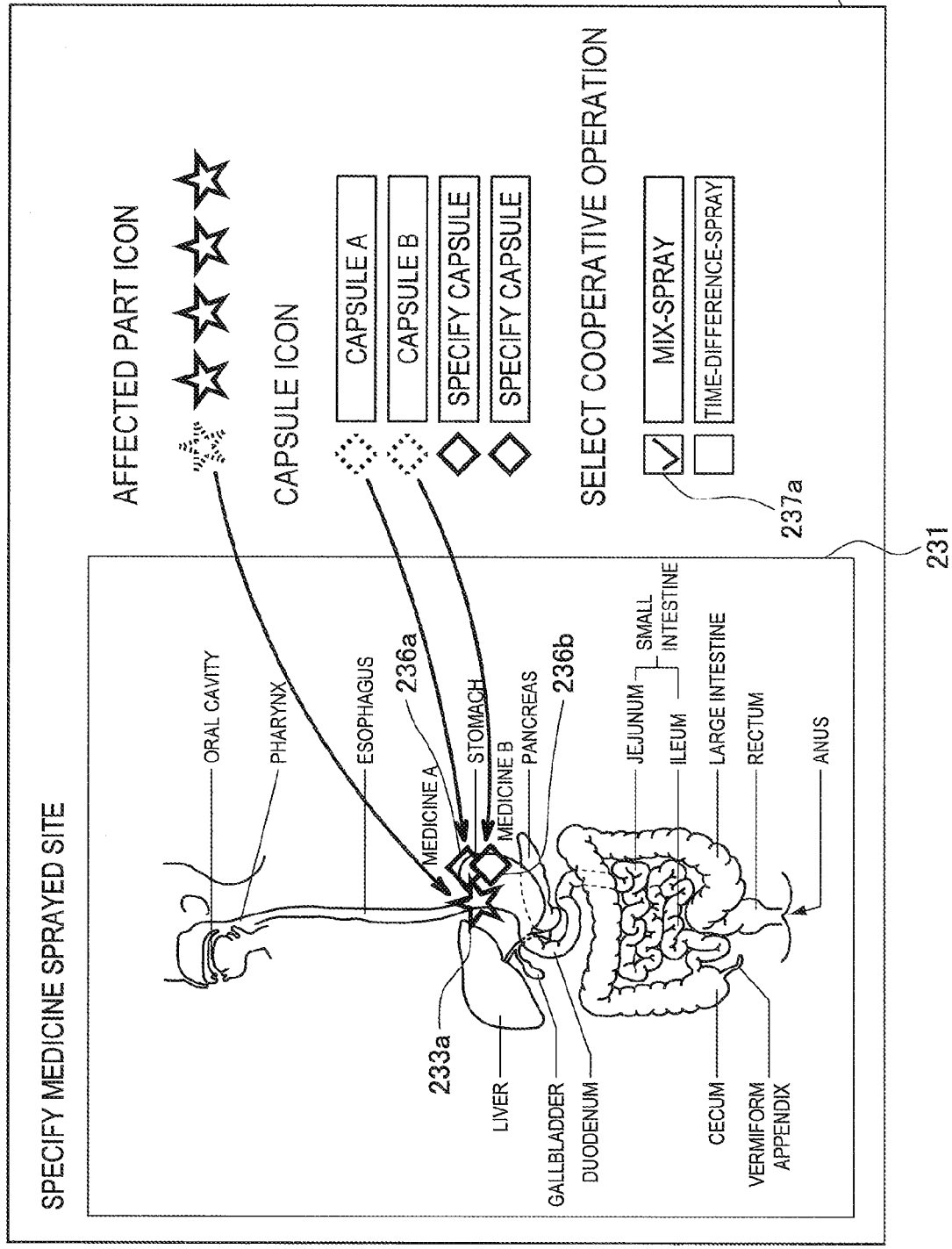
FIG. 8 is a view for describing registration of a specific site according to a first embodiment.

Next, the registration of the specific site and the specification of the capsule that is to spray the medicine to the specific site will be described with reference to FIG. 8. As shown in FIG. 8, the medical staff selects an affected part icon 233a and moves the affected part icon 233a to a desired specific site by performing a drag and drop operation.

The medical staff also specifies the plurality of capsules that are to perform cooperative operation at the specific site or in the vicinity of the specific site. Here, for example, the medical staff selects capsule icons 236a and 236b which store the medicine to be sprayed to the specific site or the vicinity of the specific site, and moves the selected capsule icons 236a and 236b to the affected part icon 233a or the vicinity of the affected part icon 233a by performing a drag and drop operation.

Further, the medical staff selects cooperative operation performed by the plurality of capsules. For example, in a case of selecting "mix-spraying" in which the plurality of capsules are caused to discharge the medicines at substantially the same time, as shown in FIG. 8, a medical staff checks the checkbox 237a.

On the basis of the input operation made by the medical staff, the control unit 21 of the control device 2 calculates the actual coordinate position in the body of the test object 3, which corresponds to the specific site on the site image 231 on which the affected part icon 233 is moved. Further, the control unit 21 memorizes the type of the capsule represented as the capsule icon 236 which is moved to the specific site or the vicinity of the specific site on the site image 231 in association with the calculated coordinate position of the specific site.

In this manner, the medical staff can specify the specific site intuitively by selecting the affected part icon 233 and the capsule icon 236 on the specification screen displayed on the display unit 23 of the control device 2, and by moving the affected part icon 233 and the capsule icon 236 to given positions on the site image 231.

As described above, in the first embodiment of the present disclosure, the control device 2 transmits an operation signal that allows the rotating magnetic field generating device 6 to generate the rotating magnetic field, and accordingly, the capsules 1A and 1B can discharge (mix-spray) the medicines A and B to the specific site at substantially the same time.

Here, although the structure of the capsules 1A and 1B is described specifically with reference to FIG. 3 to FIG. 5 in the first embodiment of the present disclosure, the structure of the capsule type medical device according to the present embodiment is not limited to the examples shown in FIG. 3 to FIG. 5. For example, the capsule type medical device according to the present disclosure may have a structure that discharges the medicine by controlling a valve that opens and closes a discharge outlet of the medicine. Accordingly, as a modification example of the first embodiment, a capsule type medical device having a structure that discharges the medicine by controlling the valve that opens and closes the discharge outlet of the medicine will be specifically described below.

(2-1-5. Modification Example 1)

A medical system according to this modification example includes a capsule type medical device 60A (hereinafter referred to as capsule 60A) storing the medicine A, a capsule type medical device 60B (hereinafter referred to as capsule 60B) storing the medicine B, and the control device 2. The capsules 60A and 60B store different medicines but have the same structure, and accordingly, the structure of the capsule 60A will be described below as an example with reference to FIG. 9.

Structure

Figure 9:
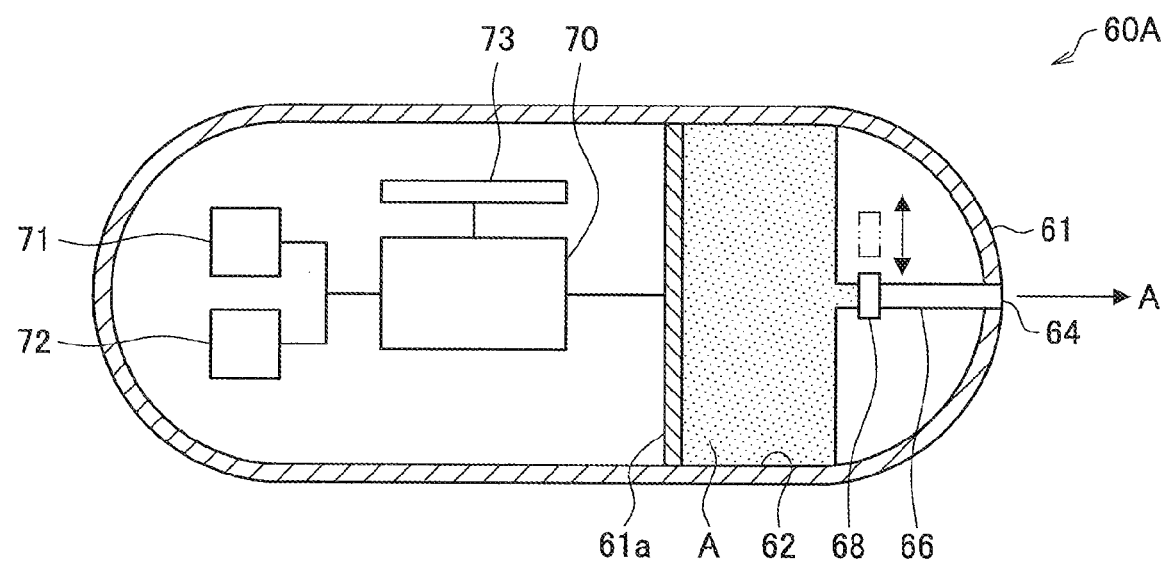
FIG. 9 shows a structure of a capsule type medical device according to a modification example 1.

FIG. 9 shows an internal structure of a main unit of the capsule 60A according to the modification example. As shown in FIG. 9, the capsule 60A according to the present embodiment includes a battery 73, a control unit 70, a reception unit 71, and a transmission unit 72 inside a capsular housing 61 and on the left side of a wall portion 61a. Note that the housing 61 is formed with plastic or the like so as to seal the inside thereof hermetically.

Further, on the right side of the wall portion 61a, a storage unit 62 storing the medicine, a medicine discharging outlet 64 formed on the outer surface of the housing 61, a medicine discharging pipeline 66 which communicates with the storage unit 62 and the medicine discharging outlet 64, and a switch valve 68 which opens and closes the pipeline 66 are provided. Note that a plurality of the medicine discharging outlets 64 may be formed around the axis of the housing 61 on one end side.

Each structural element of the capsule 60A will be described below. The battery 73 is a button-type battery, for example, and supplies power to each of the following structural elements: the control unit 70, the reception unit 71, and the transmission unit 72.

The control unit 70 has a function of controlling the whole capsule 60A. The control unit 70 (a medicine discharging unit) according to the present embodiment causes the switch valve 68 to operate in accordance with a medicine discharge signal (a control signal) received by the reception unit 71 and discharges the medicine A.

The reception unit 71 has a function of receiving data from an external device. For example, the reception unit 71 receives the medicine discharge signal from the control device 2. Further, the reception unit 71 outputs the received medicine discharge signal to the control unit 70. The transmission unit 72 has a function of transmitting data to the external device. For example, the transmission unit 72 transmits a radio wave (a position detection signal) as position information indicating the position of the capsule 1A to the control device 2. Note that in the example shown in FIG. 9, the reception unit 71 and the transmission unit 72 are shown as separate blocks; however, the structure of the capsule 60A is not limited to the example shown in FIG. 9, and may be a structure including a communication unit having a reception function and a transmission function, for example.

The storage unit 62 stores the medicine A. As shown in FIG. 9, the storage unit 62 is connected to the medicine discharging pipeline 66. As described above, the switch valve 68 which is movable so as to open and close the medicine discharging pipeline 66 is provided.

The capsule 60A having such a structure is set at such a position that the switch valve 68 closes the pipeline 66 at an initial state. Then, in accordance with the medicine discharge signal received by the reception unit 71 from the control device 2, the control unit 70 controls the switch valve 68 such that the pipeline 66 is open, and then the medicine A is discharged.

For example, in a case where the reception unit 71 has received the medicine discharge signal, the control unit 70 can control the switch valve 68 such that the medicine discharging pipeline 66 is open, and can cause the medicine A to be discharged.

The internal structure of the capsule 60A according to this modification example has been described above in detail. Next, cooperative operation according to this modification example will be described.

Cooperative Operation

Cooperative operation of the capsules 60A and 60B according to this modification example, as in cooperative operation according to the first embodiment described with reference to FIG. 6, realizes mix-spraying to the specific site by discharging the plurality of medicines at substantially the same time to the specific site.

More specifically, power is applied to each capsule 60, and each capsule 60 is introduced into the body through the mouth of the test object 3. When the power is applied, the capsule 60 starts to transmit position information to the control device 2.

Next, the control device 2 detects the position of each capsule 60 on the basis of the position information transmitted from each capsule 60. In a case where it is determined that the capsules 60A and 60B have reached the specific site or the vicinity of the specific site, the control device 2 performs broadcast transmission of the medicine discharge signal (the control signal) to each capsule 60.

Accordingly, on the basis of the control signal from the control device 2, each capsule 60 discharges the medicine to the specific site at substantially the same time, thereby realizing cooperative operation of spraying the mixed plurality of medicines.

(2-2. Second Embodiment)

The above described first embodiment is a center management type medical system in which the plurality of capsules perform cooperative operation (e.g., the mix-spraying of medicines to the specific site) under control of the control device 2 (e.g., the operation of the rotating magnetic field or the broadcast transmission of the control signal). However, the medical system according to the present disclosure is not limited to the center management type, and may be an autonomous medical system which realizes cooperative operation by the plurality of capsules performing data communication with each other, for example.

An autonomous medical system according to a second embodiment of the present disclosure will be described below. The medical system according to the present embodiment includes a plurality of capsule type medical devices. The capsule type medical devices according to the present embodiment can memorize the specific site in advance on the basis of registration of the specific site by use of the specification screen that is described above with reference to FIG. 7 and FIG. 8, and can determine whether or not the capsule type medical devices have reached the specific site or the vicinity of the specific site. In a case where the capsule type medical devices have reached the specific site or the vicinity of the specific site, the plurality of capsule type medical devices perform predetermined cooperative operation.

Here, the plurality of autonomous capsule type medical devices can perform mix-spraying of the medicines, time-difference-spraying of the medicines, playing different roles, cooperative operation in accordance with the results of treatment by the precedent capsule, and the like, as in the first embodiment. In the present embodiment, the autonomous medical system that performs time-difference-spraying will be described as an example.

Note that in a case of time-difference-spraying, unlike in "mix-spraying" described in the first embodiment, one of the plurality of capsule type medical devices needs to be suspended for a fixed time at the specific site.

Figure 11:
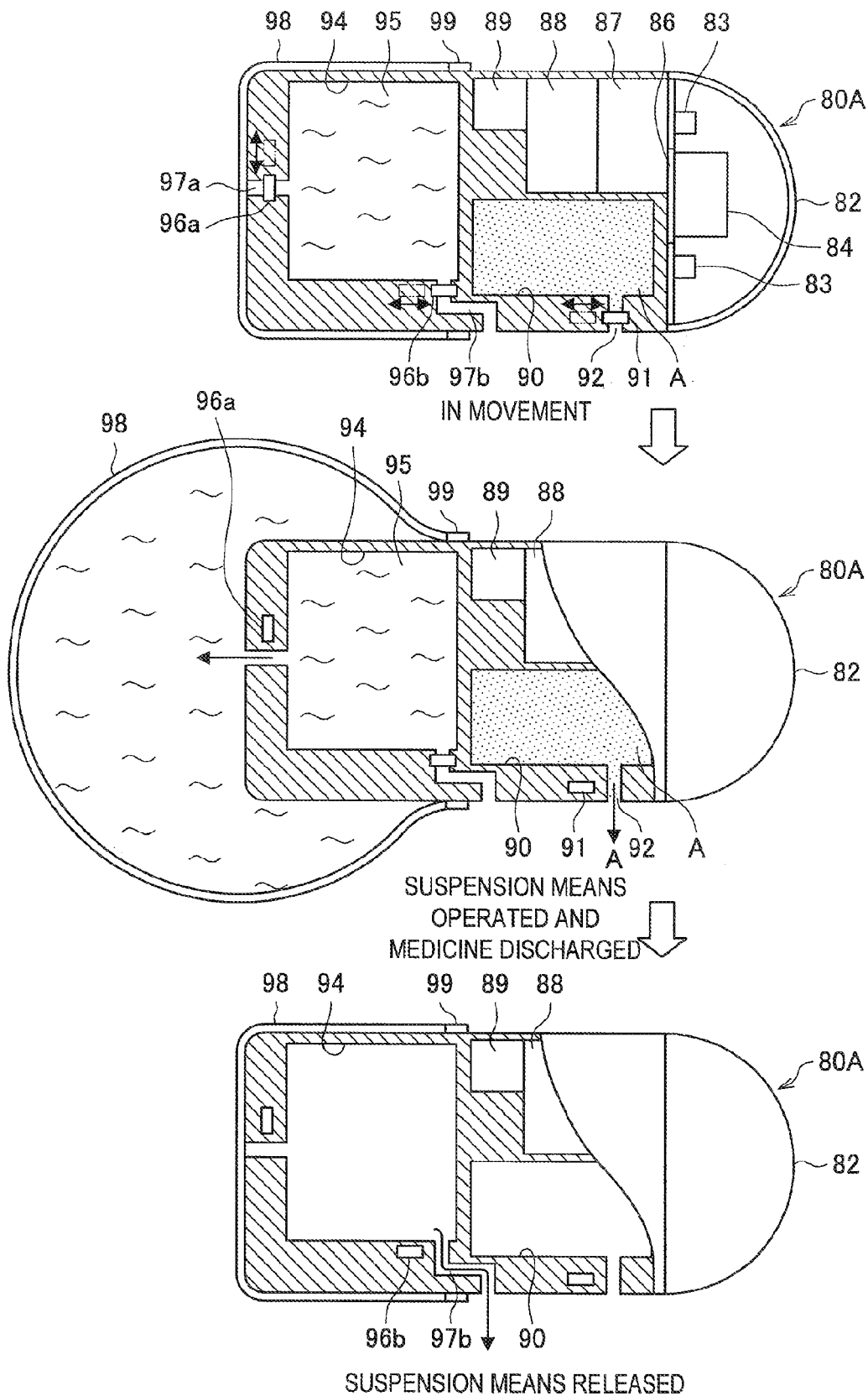
FIG. 11 shows internal structures of a capsule type medical device according to a second embodiment at a time when moving, at a time when being suspended and discharging a medicine, and at a time releasing a suspension means.

Accordingly, the capsule type medical devices according to the present embodiment include a suspension means which enables suspension for a fixed time at the specific site in the body. A capsule type medical device 80 (hereinafter referred to as capsule 80) according to the present embodiment having the suspension means will be specifically described with reference to FIG. 10 and FIG. 11. Note that each of a plurality of the capsules 80 included in the autonomous medical system according to the present embodiment is the same as a capsule 80A storing the medicine A except that the stored medicine is different, and accordingly, FIG. 10 and FIG. 11 show the capsule 80A as a representative.

FIG. 10 is an outline drawing of the capsule 80A according to the second embodiment. As shown in FIG. 10, the capsule 80A inserted into the intracelom pipeline 29 of the test object 3 has a substantially cylindrical shape, and is covered with an outer case having a curved rear end of the capsule 80A.

Further, a hemispherical transparent cover 82 is watertightly connected and secured to a tip portion of the outer case. Inside a container that is sealed hermetically inside the transparent cover 82, as will be described later, a photographing optical system and a lighting unit are disposed.

Further, an elastic and airtight balloon 98 covers a circumferential surface 81 extending from the periphery of the rear end of the capsule 80A to the vicinity of the center of the capsule 80A in the longitudinal direction. Further, the tip of the balloon 98 is airtightly secured by a belt-shape securing member 99 provided on a circumferential surface 85 of the capsule 80A.

The circumferential surface 85 includes a guide hole 97*b* through which a pressurized gas that has expended the balloon 98 is to be discharged and an opening 92 through which the medicine A stored in the capsule 80A is to be discharged.

While moving in the intracelom pipeline 29 in the state shown in FIG. 10, such a capsule 80A analyzes the photographed image photographed by the photographing optical system provided inside the transparent cover 82 and determines whether or not the capsule 80A has reached the specific site. In a case where it is determined that the capsule 80A has reached the specific site, the capsule 80A causes suspension means to operate.

Specifically, as shown in a lower part of FIG. 10, the balloon 98 is made to expand by a flow of a pressurized gas. Thus, the capsule 80 can be suspended at the specific site. The capsule 80 may discharge the medicine through the opening 92, for example, while being suspended at the specific site.

In a case of releasing the suspension means, the capsule 80 discharges the pressurized gas that has expanded the balloon 98 to the outside, so that the balloon 98 shrinks. Since the shrunk balloon 98 becomes a state shown in an upper part of FIG. 10, the capsule 80 can start to move in the intracelom pipeline 29 again.

Next, the internal structure of the capsule 80A will be specifically described with reference to FIG. 11. FIG. 11 shows internal structures of the capsule 80A according to the second embodiment at a time when moving, at a time when being suspended and discharging the medicine, and at a time when releasing the suspension means.

As shown in an upper part of FIG. 11, at a position where an image is formed in a photographing optical system 84 disposed in a center portion facing the transparent cover 82, a photographing sensor 86 such as a COMS imager (or a CCD) is disposed. Further, lighting units such as white LEDs 83 are disposed on the periphery of the photographing optical system 84.

In a backward upper portion of the photographing sensor 86, a control unit 87, a memory and communication unit 88, and a battery 89 are disposed.

The control unit 87 drives the photographing sensor 86 so that the photographing sensor 86 can photograph the inside of the body, performs signal processing of an output signal (the photographed image) of the photographing sensor 86, and controls other circuits such as the memory and communication unit 38 which will be described next.

The control unit 87 according to the present embodiment has a function of a determination unit which determines whether or not the capsule 80A has reached the specific site or the vicinity of the specific site registered in advance, on the basis of the photographed image outputted from the photographing sensor 86. Further, the control unit 87 may control switch valves 96*a* and 96*b* which will be described later so as to operate and release the suspension means. Furthermore, the control unit 87 may control a switch valve 91 which will be described later so as to discharge the medicine. Furthermore, the control unit 87 according to the present embodiment may have a function of a clocking unit which performs counting.

The memory and communication unit 88 has a function of memorizing the specific site where cooperative operation is performed and a function of communicating with the other capsule, i.e., a capsule 80B.

The battery 89 has a button shape, for example, is in conduction with a wiring substrate that is not shown, and supplies power by being electrically connected to each structural element of the capsule 80A via the wiring substrate.

A storage room 94 is provided in the backward of the battery 39 and stores a pressurized gas 95. The pressurized gas 95 is stored in the storage room 94 through an unillustrated hole communicating with the outside, and the hole is closed with a rubber stopper or the like.

The storage room 94 communicates with the balloon 98 through a guide hole 97*a*. The guide hole 97*a* is provided with the switch valve 96*a* which is controlled by the control unit 87 so as to be open and closed. As shown in a middle part of FIG. 11, in a case where the control unit 87 operates the suspension means, the control unit 87 controls the switch valve 96*a* such that the storage room 94 communicates with the balloon 98 and the pressurized gas 95 flows to the balloon 98 side. Thus, the balloon 98 expands.

Further, the storage room 94 communicates with the outside through the guide hole 97*b*. The guide hole 97*b* is provided with the switch valve 96*b* which is controlled by the control unit 87 so as to be open and closed. As shown in a lower part of FIG. 11, in a case where the suspension means is released, the control unit 87 controls the switch valve 96*b* such that the balloon 98, the storage room 94, and the outside communicate with one another. Thus, the pressurized gas 95 that has expanded the balloon 98 is discharged to the outside through the storage room 94 and the guide hole 97*b*, and the balloon 98 shrinks.

Meanwhile, a storage unit 90 is provided below the battery 39, the memory and communication unit 88, and the control unit 87, and stores the medicine A. The medicine A to be stored in the storage unit 40 is inserted therein in addition to a pressurized gas through a horizontal hole that is not shown. The horizontal hole is closed with a rubber stopper or the like after the medicine is inserted.

The storage unit 90 communicates with the outside through the opening 92. A pipeline through which the opening 92 and the storage unit 90 communicate with each other is provided with the switch valve 91 which is controlled by the control unit 87 so as to be open and closed. As shown in the middle part of FIG. 11, in a case where the control unit 87 controls discharge of the medicine, the control unit 87 controls the switch valve 92 such that the storage unit 90 communicates with the outside, and causes the medicine A to be discharged to the outside through the opening 92.

The structure of the capsule 80 according to the second embodiment has been described above. Note that the above described example shows a means that expands the balloon with the pressurized gas as the suspension means; however, the suspension means according to the present embodiment is not limited to this. For example, the capsule 80 may have an arm, and a means that causes suspension by pinching a wall portion in the body with the arm may be used. Next, cooperative operation of the plurality of capsules 80 in the autonomous medical system according to the present embodiment will be described with reference to FIG. 12. In the present embodiment, cooperative operation of time-difference-spraying of the medicine will be described as an example.

(2-2-2. Cooperative Operation)

Figure 12:
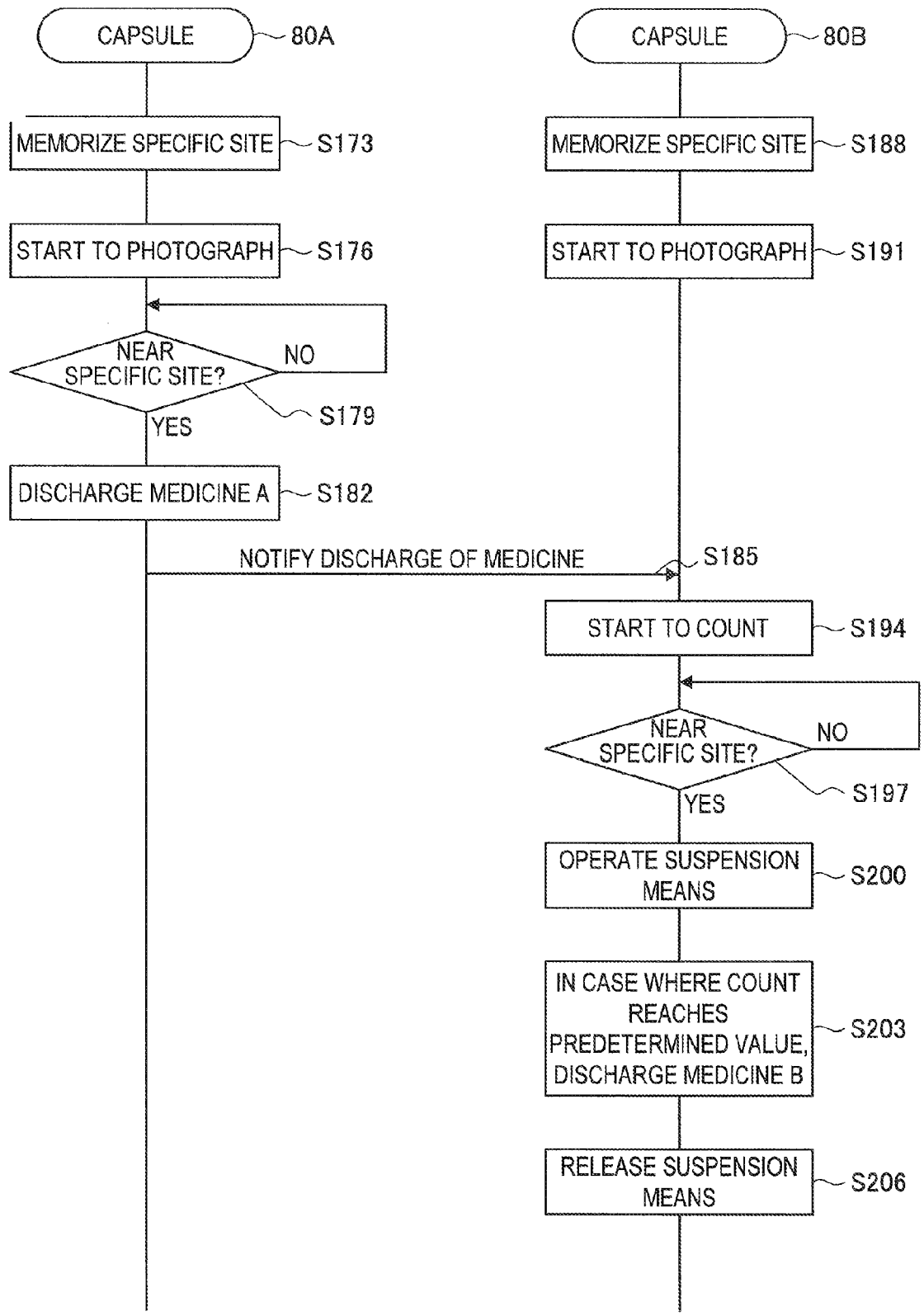
FIG. 12 is a flowchart showing cooperative operation according to a second embodiment.

FIG. 12 is a flowchart showing cooperative operation according to the second embodiment. First, as shown in FIG. 12, in steps S173 and S188, each of the capsules 80A and 80B memorizes the specific site in advance. The memorized specific site may be a site in the body, which is specified on the specification screen displayed on the display unit 23 of the control device 2, as described above.

Next, in steps S176 and S191, power is applied to the capsules 80A and 80B, and when the capsules 80A and 80B are introduced into the body of the test object 3, the capsules 80A and 80B start to photograph while moving in the body.

Next, in step S179, the capsule 80A introduced precedently into the body of the test object 3 analyzes the photographed image which is photographed while moving in the body, and determines whether or not the capsule 80A has reached the specific site or the vicinity of the specific site.

Next, in step S182, in a case where it is determined that the capsule 80A has reached the specific site or the vicinity of the specific site in the step S179, the capsule 80A discharges the stored medicine A.

Next, in step S185, the capsule 80A notifies the other capsule 80B that the capsule 80A has discharged the medicine.

Next, in step S194, when receiving the notification that the capsule 80A has discharged the medicine, the capsule 80B starts to count.

Further, in step S197, the capsule 80B analyzes the photographed image photographed while moving in the body, and determines whether or not the capsule 80B has reached the specific site or the vicinity of the specific site.

Next, in step S200, in a case where it is determined that the capsule 80B has reached the specific site or the vicinity of the specific site in the step S197, the capsule 80B operates the suspension means. Specifically, the capsule 80B controls the switch valve 96*a* such that the pressurized gas 95 flows to the balloon 98 to expand the balloon 98, thereby suspending the capsule 80B at the specific site in the intracelom pipeline 29, as shown in the lower part of FIG. 10.

Next, in step S203, in a case where the count reaches a predetermined value, the capsule 80B discharges the stored medicine B. In this manner, the plurality of medicines can be discharged to the specific site in a time difference manner, enabling more effective treatment.

Then, in step S206, the capsule 80B releases the suspension means. Specifically, the capsule 80B causes the balloon 98 to shrink by controlling the switch valve 96*b* such that the pressurized gas 95 that has expanded the balloon 98 is discharged to the outside. Thus, the capsule 80B can move in the intracelom pipeline 29 again, as shown in the upper part of FIG. 10.

As described above, the medical system according to the second embodiment enables autonomous cooperative operation on the basis of data communication between the plurality of capsules 80.

(2-2-3. Modification Example 2)

In the second embodiment described above, as in the first embodiment, the plurality of capsules are introduced into the body of the test object 3, so that a burden may be imposed on the test object 3. Accordingly, as a modification example of the second embodiment, a separable capsule type medical device 100 (hereinafter referred to as capsule 100) is proposed.

Thus, the test object 3 may only have to swallow a single capsule 100 and the capsule 100 is separated into a plurality of capsules 100A and 100B in the body, thereby realizing cooperative operation. Here, a configuration of the separable capsule 100 according to a modification example 2 will be specifically described with reference to FIG. 13.

Configuration

Figure 13:
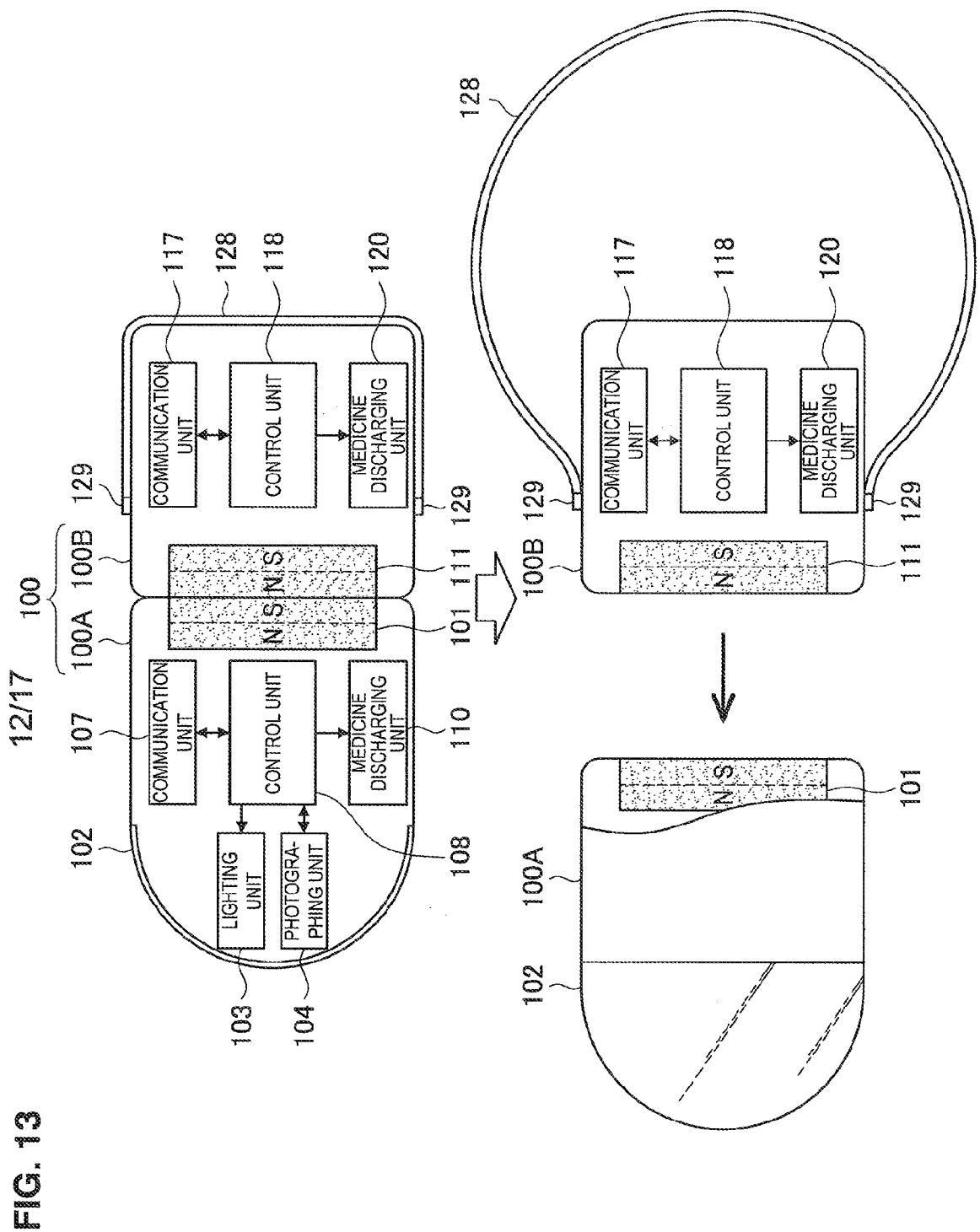
FIG. 13 shows a structure of a separable capsule type medical device according to a modification example 2.

As shown in FIG. 13, in the capsule 100, the capsules 100A and 100B are connected to each other in a separable manner. Note that a configuration of a connecting part of the capsules 100A and 100B is not particularly limited, and in the example shown in FIG. 13, electromagnets 101 and 111 connect the capsules 100A and 100B to each other as an example. Alternatively, the connecting part may be achieved by a substance that can be dissolved in the body.

As shown in FIG. 13, the capsule 100A includes the electromagnet 101, a lighting unit 103, a photographing unit 104, a control unit 108, a communication unit 107, and a medicine discharging unit 110. The lighting unit 103 and the photographing unit 104 are disposed inside a transparent cover 102 and photograph the inside of an intracelom pipeline when the capsule 100 moves inside the body.

The control unit 108 can analyze the photographed image of the inside of the body, the photographed image being outputted from the photographing unit 104, and can determine whether or not the capsule 100 has reached the specific site that is registered in advance.

The medicine discharging unit 110 performs control such that the medicine A stored in a storage unit that is not shown is discharged to the outside of the capsule 100A.

The communication unit 107 performs data communication with the capsule 100B. Specifically, for example, the communication unit 107 notifies the capsule 100B that the capsule 100 has reached the specific site and that medicine discharging unit 110 has discharged the medicine A.

Meanwhile, as shown in FIG. 13, the capsule 100B includes the electromagnet 111, a control unit 118, a communication unit 117, and a medicine discharging unit 120. Further, an elastic and airtight balloon 128 covers a circumferential surface extending from the periphery of the rear end of the capsule 100B to the vicinity of the center of the capsule 100B in the longitudinal direction. Further, the tip of the balloon 128 is airtightly secured by a belt-shape securing member 129 provided on the circumferential surface of the capsule 100B.

The communication unit 117 performs data communication with the capsule 100A. Specifically, for example, the communication unit 117 receives a notification that the capsule 100 has reached the specific site and that the capsule 100A has discharged the medicine.

When the communication unit 117 receives the notification that the capsule 100 has reached the specific site, the control unit 118 operates the suspension means. Specifically, for example, the control unit 118 flows a pressurized gas stored in a storage room that is not shown to the balloon 128 to expand the balloon, and suspends the capsule 100 at the specific site or in the vicinity of the specific site. Further, the control unit 118 releases the suspension means after the medicine discharging unit 120, which will be described later, discharges the medicine. Specifically, for example, the control unit 118 discharges the pressurized gas that has expanded the balloon 128 to the outside of the capsule 100B through a guide hole that is not shown, so that the balloon 128 shrinks.

Further, when the communication unit 117 receives the notification that the capsule 100A has discharged the medicine, the control unit 118 performs control such that the capsule 100A is separated. More specifically, for example, the control unit 118 can switch the polarity of the electromagnet 111 to separate the capsule 100A.

Further, when the communication unit 117 receives the notification that the capsule 100A has discharged the medicine, the control unit 118 starts to count.

In a case where the count counted by the control unit 118 reaches a predetermined value, the medicine discharging unit 120 performs control such that the medicine B stored in a storage unit that is not shown is discharged to the outside of the capsule 100B.

Cooperative Operation

Cooperative operation of the capsules 100A and 100B according to this modification example realizes time-difference-spraying to the specific site by discharging the plurality of medicines to the specific site in a time difference manner, as in cooperative operation according to the second embodiment which has been described above with reference to FIG. 12.

Figure 14:
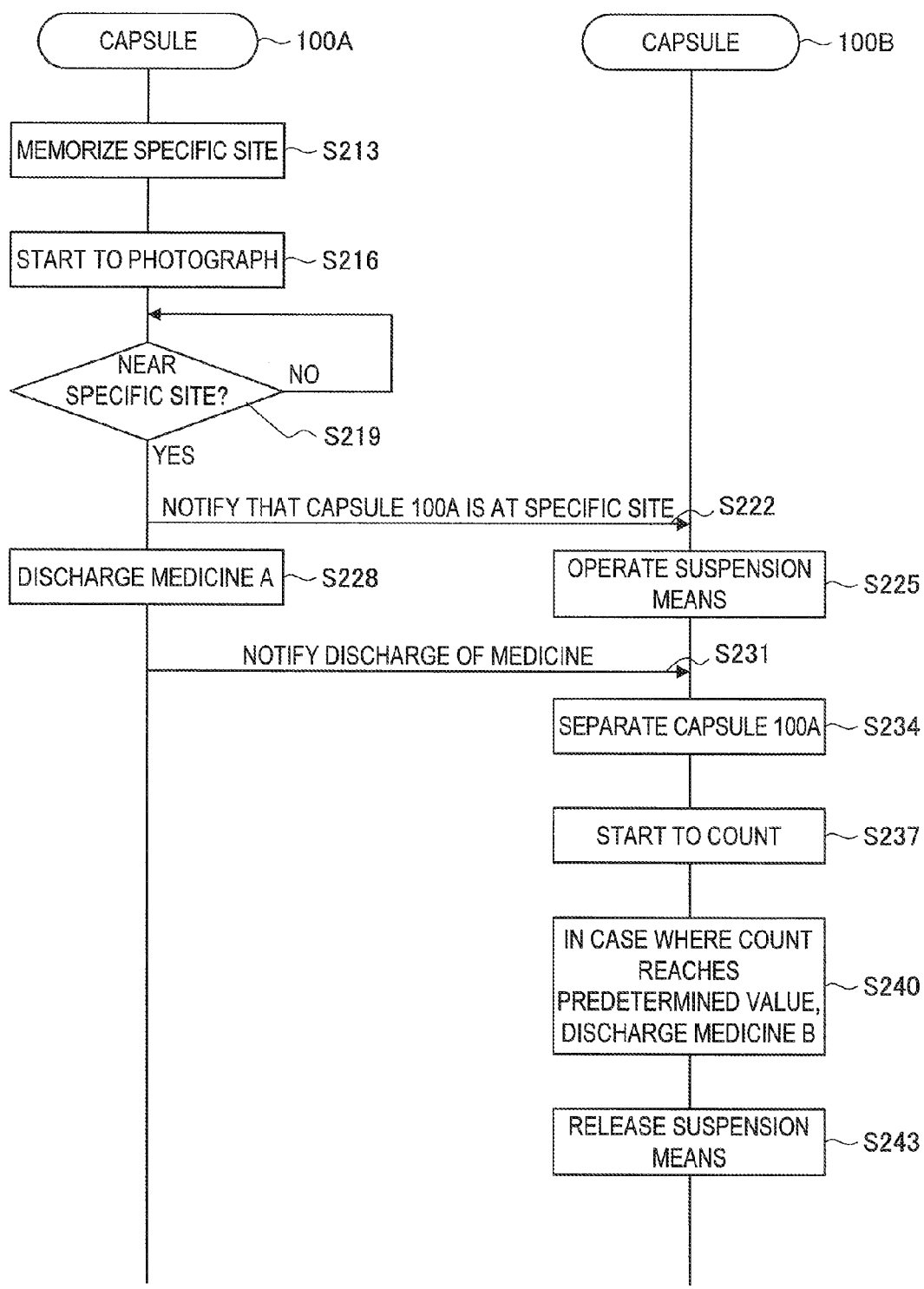
FIG. 14 is a flowchart showing cooperative operation according to a modification example 2.

As shown in FIG. 14, first, in step S213, the control unit 108 of the capsule 100A memorizes the specific site in advance. The memorized specific site may be a site in the body, which is specified on the specification screen displayed on the display unit 23 of the control device 2, as described above.

Next, in step S213, power is applied to the capsule 100, and when the capsule 100 is introduced into the body of the test object 3, the photographing unit 104 of the capsule 100 starts to photograph while moving in the body.

Next, in step S219, the control unit 108 of the capsule 100A analyzes the photographed image which is photographed while moving in the body, and determines whether or not the capsule 100 has reached the specific site or the vicinity of the specific site.

Next, in step S222, in a case where it is determined that the capsule 100A has reached the specific site or the vicinity of the specific site in the step S219, the capsule 100A notifies the connected capsule 100B that the capsule 100A has reached the specific site or the vicinity of the specific site.

Next, in step S225, the capsule 100B connected to the capsule 100A operates the suspension means, so that the capsule 100 is suspended at the specific site. Specifically, as described above, the capsule 100B flows a pressurized gas to the balloon 128 to expand the balloon 128, thereby suspending the capsule 100 at the specific site or in the vicinity of the specific site, as shown in a lower part of FIG. 13.

Next, in step S228, the capsule 100A discharges the stored medicine A. Next, in step S231, the capsule 100A notifies the connected capsule 100B that the capsule 100A has discharged the medicine.

Next, in step S234, the capsule 100B which has received the notification that the medicine has been discharged performs control such that the capsule 100A is separated. Specifically, as described above, the capsule 100B can separate the capsule 100A by switching the polarity of the electromagnet 111, as shown in the lower part of FIG. 13.

Next, in step S237, the capsule 100B starts to count.

Next, in step S240, in a case where the count reaches a predetermined value, the capsule 100B discharges the stored medicine B. In this manner, the plurality of medicines can be sprayed to the specific site in a time difference manner, enabling more effective treatment.

Then, in step S243, the capsule 100B releases the suspension means. Specifically, as described above, the capsule 100B causes the balloon 128 to shrink by discharging the pressurized gas that has expanded the balloon 128 to the outside through a guide hole that is not shown. Thus, the capsule 100B can move in the body again.

(2-3. Third Embodiment)

As for the medical systems described above according to the first and second embodiment, mix-spraying and time-difference-spraying of the medicine have been described as examples of cooperative operation; however, cooperative operation that can be realized by the medical system according to the present disclosure is not limited thereto. For example, in an autonomous medical system according to the present disclosure, cooperative operation may be performed by two capsule type medical devices having a plurality of functions playing different roles. A third embodiment in which such cooperative operation in which different roles are played will be specifically described below, by giving a plurality of examples.

(2-3-1. First Role Allotment)

As first role allotment, a case is given in which a lighting role and a photographing role are allocated between a plurality of capsules 200A and 200B having a lighting function and a photographing function. A plurality of capsule type medical devices which realize the first role allotment and cooperative operation thereof will be described below sequentially with reference to FIG. 15 to FIG. 17.

Configuration

Figure 15:
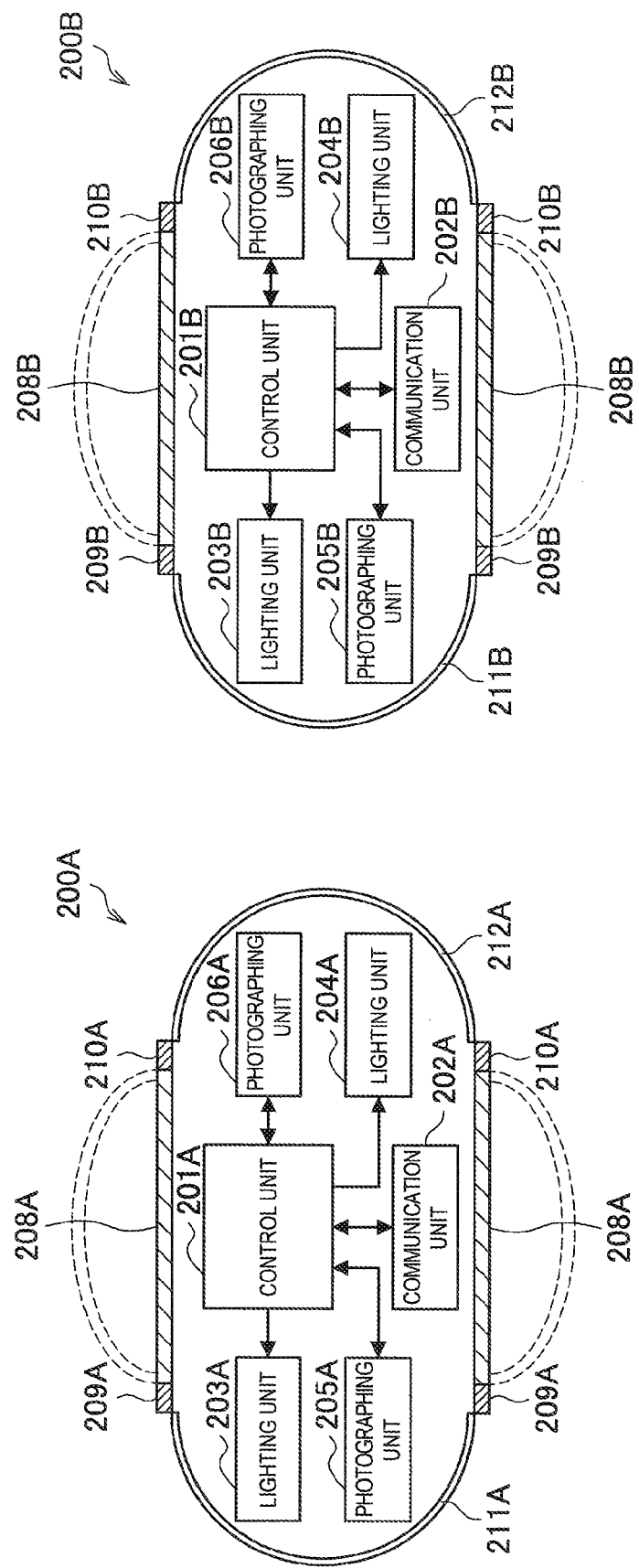
FIG. 15 is a block diagram showing configurations of capsules having a photographing function and a lighting function according to a third embodiment.

FIG. 15 is a block diagram showing configurations of the capsules 200A and 200B having the photographing function and the lighting function according to the third embodiment. Note that since the structures of the capsules 200A and 200B are the same, in a case where the capsules 200A and 200B do not need to be distinguished from each other, each of the capsules 200A and 200B is referred to as capsule 200. Further, in a case where reference numerals of structural elements do not need to be distinguished from each other, alphabetical characters A and B are omitted.

As shown in FIG. 15, the capsule 200 includes a control unit 201, a communication unit 202, lighting units 203 and 204, and photographing units 205 and 206.

The lighting unit 203 and the photographing unit 205 are disposed inside a transparent cover 211 provided at the tip of the capsule 200, and the lighting unit 204 and the photographing unit 206 are disposed inside a transparent cover 212 provided at the rear end of the capsule 200.

The control unit 201 controls each structural element of the capsule 200. More specifically, the control unit 201 can determine whether or not the capsule 200 has reached the specific site by analyzing the photographed image of the inside of the body, the photographed image being photographed by the photographing units 205 and 206. Further, the control unit 201 may perform control such that photographing timing of the photographing units 205 and 206 and lighting timing of the lighting units 203 and 204 cooperate with the other capsule 200.

The control unit 201 memorizes the photographed image photographed by cooperation with the other capsule 200 at the specific site or in the vicinity of the specific site in a memory unit that is not shown.

The communication unit 202 performs data communication between the plurality of capsules 200. Specifically, for example, the communication unit 202 notifies the other capsule 200 that photographing is to be performed.

As shown in FIG. 15, an elastic and airtight balloon 216 covers a central circumferential surface of the capsule 200 in the longitudinal direction. Both ends of a balloon 208 are airtightly secured by belt-shape securing members 209 and 210 provided on the circumferential surface of the capsule 200.

The control unit 201 operates the suspension means such that a pressurized gas stored in a storage room that is not shown flows to the balloon 208 to expand the balloon 208 and suspend the capsule 200 at a predetermined site. When the control unit 201 releases the suspension means, the pressurized gas that has expanded the balloon 208 is discharged to the outside of the capsule 200 through a guide hole that is not shown, so that the balloon 208 shrinks and the capsule 200 can move in the body again.

Cooperative Operation

Figure 16:
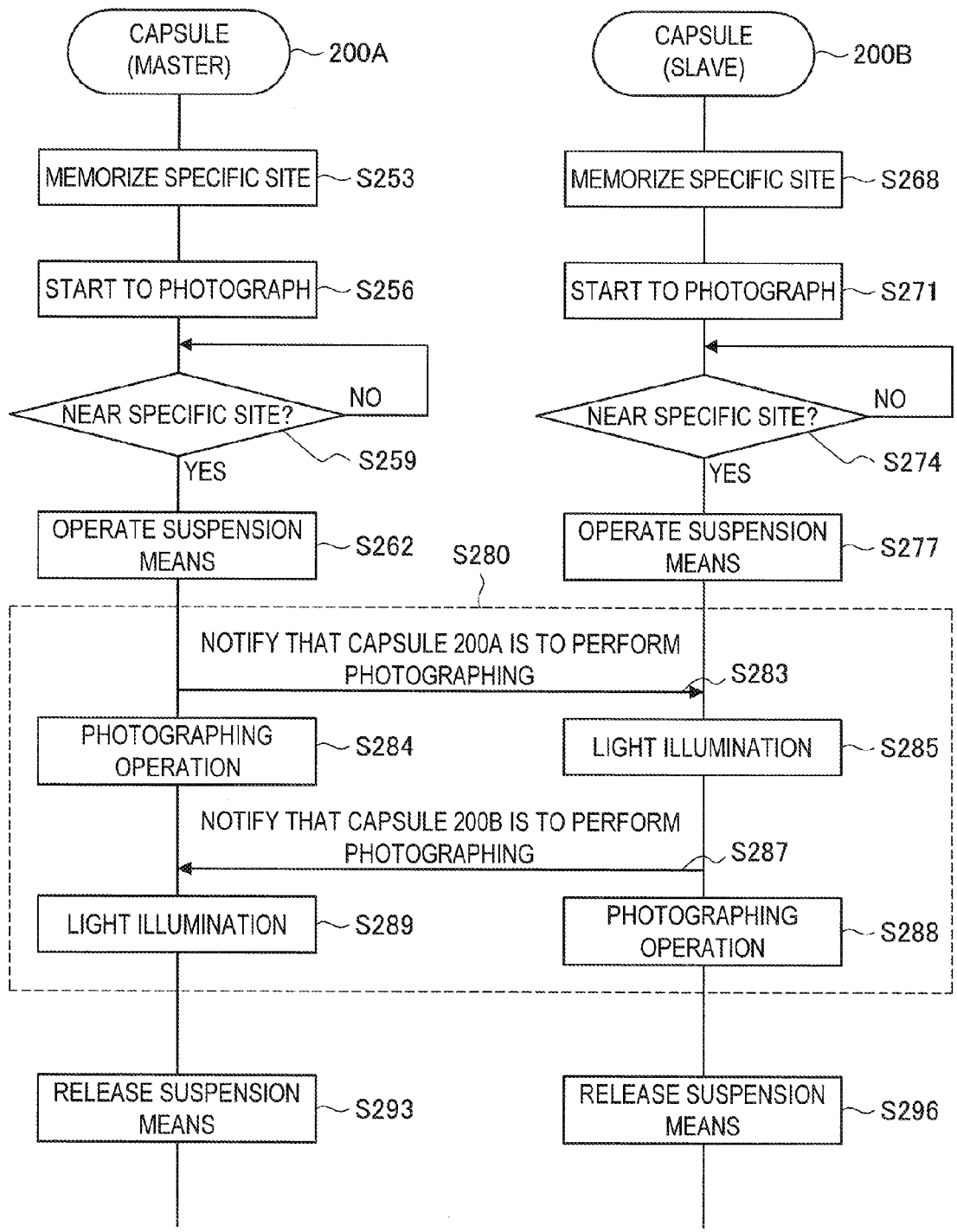
FIG. 16 is a flowchart showing cooperative operation of a plurality of capsules having a photographing function and a lighting function according to a third embodiment.

Next, cooperative operation of the capsules 200A and 200B will be described with reference to FIG. 16. FIG. 16 is a flowchart showing cooperative operation in the first role allotment. Here, as described above, although the capsules 200A and 200B have the same configuration, the capsule 200A to be swallowed by the test object 3 precedently is referred to as master, and the following capsule 200B is referred to as slave.

As shown in FIG. 16, first, in steps S253 and S268, the capsules 200A and 200B memorize the specific site in advance. The memorized specific site may be a site in the body, which is specified on the specification screen displayed on the display unit 23 of the control device 2, as described above.

Next, in steps S256 and S271, power is applied to the capsules 200A and 200B, and when the capsules 200A and 200B are introduced into the body of the test object 3, the capsules 200A and 200B start to photograph while moving in the body.

Next, in steps S259 and S274, the capsules 200A and 200B analyze the photographed image which is photographed while moving in the body, and determine whether or not the capsules 200A and 200B have reached the specific site or the vicinity of the specific site.

Next, in steps S262 and 277, in a case where it is determined that the capsules 200A and 200B have reached the specific site or the vicinity of the specific site in the steps S259 and S274, the capsules 200A and 200B operate the suspension means to be suspended at the specific site or in the vicinity of the specific site.

Next, in step S280, the capsules 200A and 200B perform data communication with each other, and performs cooperative operation by switching photographing operation and illumination lighting.

Specifically, in step S283, first, the capsule 200A (master) notifies the capsule 200B (slave) that the capsule 200A is to perform photographing. Next, in step S284, the capsule 200A (master) performs photographing operation; meanwhile, in step S285, 200B (slave) which has received the notification of photographing performs controls so as to light illumination.

Next, in step S287, the capsule 200B (slave) notifies the capsule A (master) that the capsule 200B is to perform photographing. Next, in step S288, the capsule 200B (slave) performs photographing operation; meanwhile, in step S289, 200A (master) which has received the notification of photographing performs control so as to light illumination.

Here, as described above with reference to FIG. 15, the capsules 200 have the plurality of photographing units 205 and 206 and the plurality of lighting units 203 and 204. Therefore, photographing is performed by use of the same combination by the capsules 200A and 200B repeating the steps S283 to S289.

FIG. 17 shows an example of combination of photographing operation and illumination lighting performed by the capsules 200A and 200B according to the present embodiment. FIG. 17 is a table showing combination of cooperative operation of photographing and lighting according to the third embodiment.

First, in a case where the capsule 200A plays a photographing role and the capsule 200B plays a lighting role, as shown in FIG. 17, the photographing unit 205A of the capsule 200A performs photographing at timing when the lighting unit 203B of the capsule B is turned on and when the lighting unit 204B is turned on.

In a similar manner, as shown in FIG. 17, the photographing unit 206A of the capsule 200A performs photographing at timing when the lighting unit 203B of the capsule B is turned on and when the lighting unit 204B is turned on.

Accordingly, the capsule 200A can obtain four photographed images in total. Next, role allotment of the capsule 200A and the capsule 200B is switched, so that the capsule 200A plays the lighting role and the capsule 200B plays the photographing role.

As shown in FIG. 17, the photographing unit 205B of the capsule 200B performs photographing at timing when the lighting unit 203A of the capsule A is turned on and when the lighting unit 204A is turned on.

In a similar manner, as shown in FIG. 17, the photographing unit 206B of the capsule 200B performs photographing at timing when the lighting unit 203A of the capsule A is turned on and when the lighting unit 204A is turned on.

Accordingly, the capsule 200B can obtain four photographed images in total.

As described above, in a case where the photographing role and the lighting role are allocated between the capsules 200A and 200B by use of the same combination shown in FIG. 17, no matter which direction the capsules 200A and 200B face, high quality photographed images can be obtained.

(2-3-2. Second Role Allotment)

Next, an example of second role allotment according to the present embodiment will be described. As the second role allotment, a case is given in which a marker role and a photographing role are allocated between a plurality of capsules 220A and 220B having a marker function and the photographing function. Configurations of a plurality of capsule type medical devices which realize the second role allotment and cooperative operation thereof will be described below sequentially with reference to FIG. 18 and FIG. 19.

Configuration

Figure 18:
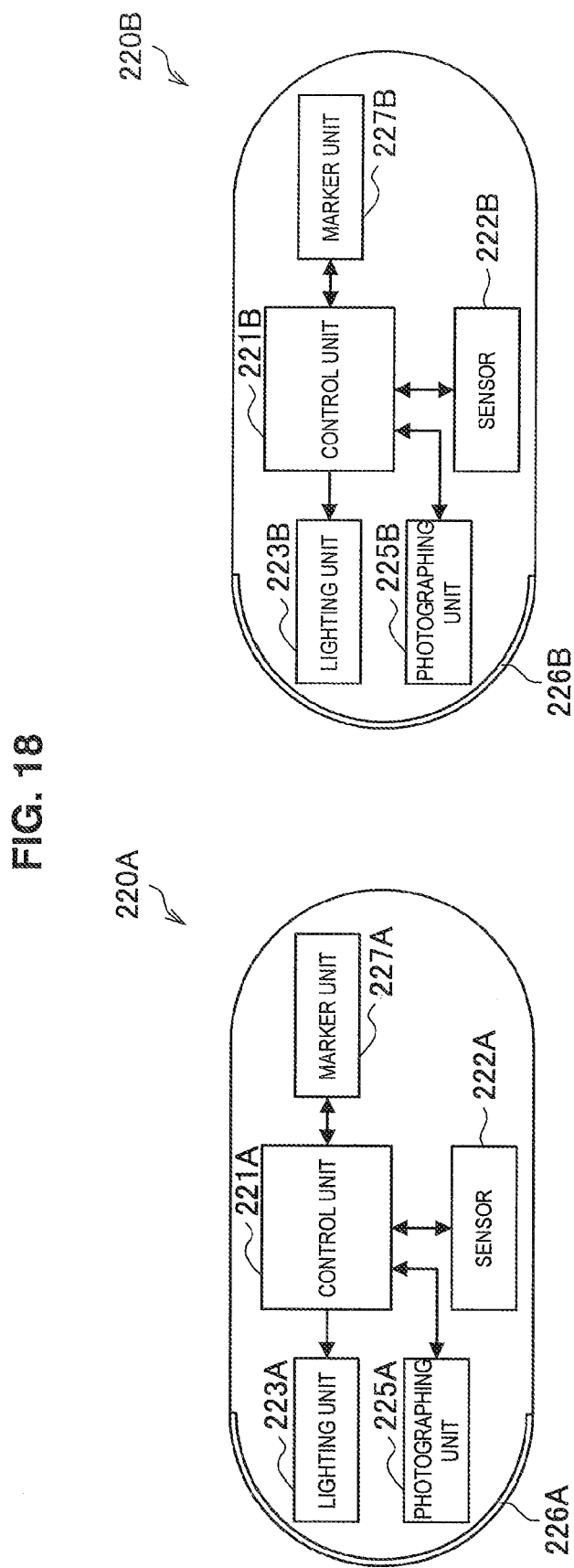
FIG. 18 is a block diagram showing configurations of capsules having a marker function and a photographing function according to a third embodiment.

FIG. 18 is a block diagram showing configurations of the capsules 220A and 220B having the marker function and the photographing function according to the third embodiment. Note that since the structures of the capsules 220A and 220B are the same, in a case where the capsules 220A and 220B do not need to be distinguished from each other, each of the capsules 220A and 220B is referred to as capsule 200. Further, in a case where reference numerals of structural elements do not need to be distinguished from each other, alphabetical characters A and B are omitted.

As shown in FIG. 18, a capsule 220 includes a control unit 221, a sensor 222, a lighting unit 223, a photographing unit 225, and a marker unit 227.

The lighting unit 223 and the photographing unit 225 are disposed inside a transparent cover 226 provided at the tip of the capsule 220.

The control unit 221 controls each structural element of the capsule 220. More specifically, the control unit 221 can determine whether or not the capsule 220 has reached the specific site by analyzing the photographed image of the inside of the body, the photographed image being photographed by the photographing unit 225.

In a case where it is determined that the capsule 220 has reached the specific site or the vicinity of the specific site, the control unit 221 may perform control such that the marker unit 227 marks the specific site.

In a case where the sensor 222 detects the marking, the control unit 221 may control the photographing unit 225 and the lighting unit 223 such that a site where the marking has been detected (the specific site) is be photographed.

The marker unit 227 marks the specific site or the vicinity of the specific site in a case where the control unit 221 determines that the capsule 220 has reached the specific site or the vicinity of the specific site. The marker unit 227 may be a "clipping device" disclosed in the above described Patent Literature 2 (JP 2005-334331A), for example. The clipping device can be attached such that a metal clip (a marker) pinches a biological tissue.

The sensor 222 is a detection unit which detects the marker given to the inside of the body. The sensor 222 may be a "metal sensor" disclosed in the above described Patent Literature 2, for example. The metal sensor can detect the metal clip (the marker) attached to the specific site or the vicinity of the specific site, as described in the Patent Literature 2. Further, the sensor 222 may be an image sensor that detects specular reflection from the clip (the marker) from an image, instead of the metal sensor.

Note that, as a marker, the marker unit 227 may inject an isotope, a fluorescent agent, a magnetic fluid, or the like, or scatter pigment, for example. In such a case, the sensor 222 is a radiation sensor that detects radiation, an image sensor that detects the fluorescence from an image, a magnetic sensor that detects the magnetic fluid, an image sensor that detects the color or brightness of the pigment from an image, or the like.

Cooperative Operation

As described above, the capsules 220A and 220B which realize the second role allotment have the photographing function and the marker function. In this case, each of the control units 221A and 221B may perform control such that the capsule 220A (master) swallowed by the test object 3 precedently plays the marking role and the following capsule 220B (slave) plays the photographing role.

The capsule 220A (master) determines whether or not the capsule 220A (master) is at the specific site or in the vicinity of the specific site that is memorized in advance, on the basis of the photographed image of the inside of the body, the image being photographed while the capsule 220A (master) moves in the body. Further, in a case where the capsule 220A (master) is at the specific site or in the vicinity of the specific site, the capsule 220A (master) gives a marker (marks) the specific site or the vicinity of the specific site by use of the marker unit 227A.

Next, the capsule 220B (slave) which is swallowed by the test object 3 after the capsule 220A detects the marker by use of the sensor 222 while moving in the body. In a case where the capsule 220B detects the marker by use of the sensor 222B, the capsule 220B controls the photographing unit 225B and the lighting unit 223B and photographs a site or the vicinity of the site where the marker has been detected (the specific site or the vicinity of the specific site).

As described above, the capsules 220A and 220B having the marker function and the photographing function can perform cooperative operation by playing the marker (marking) role of giving a marker to the specific site and by playing the photographing role of photographing the specific site.

(2-3-3. Third Role Allotment)

As third role allotment, a case is given in which a plurality of capsules having the marker function and a medicine discharging function play the marker role and a medicine discharging role. A plurality of capsule type medical devices which realize such third role allotment has a configuration obtained by adding a medicine discharging unit to the configuration of the capsule 220 shown in FIG. 18.

Further, in cooperative operation performed by the plurality of capsule type medical devices which realize the third role allotment, the process in which one of the capsules (master), which is swallowed by the test object 3 precedently, marks the specific site or the vicinity of the specific site is the same as that in cooperative operation in the second role allotment described above.

Next, the other capsule (slave), which is swallowed by the test object 3 after the one of the capsules, detects the marker by use of the sensor while moving in the body, and discharges the medicine at the detected portion (to the specific site or the vicinity of the specific site).

As described above, the plurality of capsules having the marker function and the medicine discharging function can perform cooperative operation by playing the marker (making) role of giving the marker to the specific site and a medicine discharging role of discharging the medicine to the specific site.

(2-3-4. Fourth Role Allotment)

As fourth role allotment, a plurality of capsules having a function of extracting a biological tissue from the inside of the body of the test object 3 may perform cooperative operation by playing a role of extracting the biological tissue precedently and a role of extracting the biological tissue later.

A plurality of capsule type medical devices which realize such fourth role allotment include an extraction unit instead of the sensor 222 and the marker unit 227 of the capsule 220 shown in FIG. 18.

The extraction unit can extract a biological tissue having such a size that is necessary for biological testing. The extraction unit may be a "cut extraction unit" disclosed in JP 2009-131415A (hereinafter referred to as Patent Literature 3), for example. The cut extraction unit is, as disclosed in Patent Literature 3, a cutting tool (a cutting unit) having a blade formed into a V-shape, for example. The cutting tool is exposed from an opening of a capsule and secured and disposed such that the blade is directed to the circumferential direction of the capsule. Further, when the cutting unit rotates around the circumferential direction of the capsule together with the capsule, the biological tissue is cut and extracted to the inside through the opening.

Further, in cooperative operation performed by the plurality of capsule type medical devices which realize the fourth role allotment, first, one of the capsules (master) swallowed by the test object 3 precedently extracts the biological tissue from a first specific site or the vicinity of the first specific site, and notifies the other capsule (slave) that the extraction has been completed.

When the other capsule (slave) swallowed by the test object 3 after the one of the capsules (master) receives the notification of the completion of extraction from the master capsule, the other capsule extracts the biological tissue from a second specific site or the vicinity of the second specific site.

In this manner, in the fourth role allotment, the plurality of capsules can perform extraction of biological tissues in cooperation with each other on the basis of data communication between the capsules.

<3. Conclusion>

As described above, in the medical system according to the present embodiment, cooperative operation of the plurality of capsule type medical devices enables more effective treatment.

More specifically, for example, cooperative operation is performed such that the plurality of capsules discharge the respective medicines at substantially the same time to the same specific site or the vicinity of the specific site, thereby enabling mix-spraying of the plurality of medicines.

Further, cooperative operation is performed such that the plurality of capsules discharge the respective medicines in a time difference manner to the same site or the vicinity of the specific site, thereby enabling spraying of the medicines at more effective timings.

In a case where the plurality of capsules have a plurality of functions, the capsule that is swallowed by the test object 3 precedently is set as a master and the capsule that is swallowed later is set as a slave, thereby enabling cooperative operation with role allotment.

In a case where the capsule according to the present embodiment can be separated, the capsule may be separated into a plurality of capsules after being swallowed by the test object 3, and the plurality of capsules can perform cooperative operation.

The preferred embodiments of the present invention have been described above with reference to the accompanying drawings, whilst the present invention is not limited to the above examples, of course. A person skilled in the art may find various alterations and modifications within the scope of the appended claims, and it should be understood that they will naturally come under the technical scope of the present invention.

For example, in the separable capsule 100 which has been described with reference to FIG. 13, each of 100A and 100B included in the capsule 100 has the same function (the medicine discharging unit); however, variations of functions included in the separable capsule are not limited thereto. For example, a combination of 100A having the marker unit and 100B having the sensor and the photographing function or a combination of 100A having the medicine discharging unit and 100B having the photographing function may be used.

In a case of the combination of 100A having the medicine discharging unit and 100B having the photographing function, after 100A discharges the medicine to the specific site and 100A is separated, after a predetermined time passes, 100B may photograph the specific site. Thus, a progress of the specific site after the medicine is sprayed (after treatment) can be observed.

Further, in a case where a plurality of capsules have the same function such as discharging the medicine, the following capsule may control treatment in accordance with the results of treatment performed by the precedent capsule. More specifically, in a case where the precedent capsule fails to discharge the medicine, for example, the following capsule may discharge the medicine. Further, the following capsule may include a diagnosis unit and diagnose the progress after the precedent capsule has discharged the medicine, in order to control whether or not the medicine is discharged.

Note that the diagnosis unit may diagnose on the basis of the photographed image or the extracted biological tissue. Further, the diagnosis unit may diagnose on the basis of a predetermined value (e.g., a pH level) detected by a sensor that detects the status inside the body.

Further, in the medical system according to the present disclosure, the weight of the plurality of capsules may be changed. Thus, the order of capsules can be controlled even in a stomach. Accordingly, for example, even in a case where the precedently swallowed capsule (master) and the later swallowed capsule (slave) play different roles, the order of capsules can be set to be a right order in the stomach, which is effective.

Further, in the third embodiment, the case where cooperative operation is performed by the two capsule type medical devices having the same function play different roles has been described; however, cooperative operation according to the present disclosure is not limited thereto. For example, two capsule type medical devices having different functions may perform cooperative operation. More specifically, a capsule having a photographing function and a capsule having a lighting function may perform data communication with each other, and when the capsule having the photographing function photographs, the capsule having the lighting function may operate to light illumination. Alternatively, a capsule having a function of giving a marker and a capsule having a marker detecting function and a medicine discharging function may operate in cooperation with each other. Further alternatively, a capsule having a function of giving a marker and a capsule having a marker detecting function and a photographing function may operate in cooperation with each other.

As for a method of controlling the order of a plurality of capsules moving in the body, other than changing the weight, the size or the shape (e.g., a sphere, a polyhedron, or the presence or absence of a projection) of the capsules may be changed to control the order.

Further, as described above with reference to FIG. 1, the capsule 1 and the control device 2 perform data communication with each other via the extracorporeal unit 7; however, the medical system according to the present embodiment is not limited thereto. For example, the capsule 1 and the control device 2 may perform data communication directly with each other.

Furthermore, the photographed image of a site in the body, which is photographed by the photographing unit included in the capsule in each embodiment, may be used for measuring the effects of medication.

The invention claimed is:
1. A medical system, comprising:
 a first capsule type medical device including a first medicine stored in a first storage unit;
 a control device coupled to the first capsule medical device; and
 a second capsule type medical device coupled to the control device, wherein the second capsule type medical device includes a second medicine stored in a second storage unit, wherein the second medicine is to be mixed with the first medicine,
 wherein the control device is configured to control cooperative operation of the first and second capsule type medical devices to mix the first medicine and the second medicine at a specific site in a body.
2. The medical system according to claim 1,
 wherein each of the first and second capsule type medical devices includes
  a medicine discharging unit, wherein a first medicine discharging unit of the first capsule type medical device is configured to control discharge of the first medicine stored in the first storage unit, and wherein a second medicine discharging unit of the second capsule type medical device is configured to control discharge of the second medicine stored in the second storage unit, and
 wherein the first and second capsule type medical devices are configured to discharge the first and second medicines respectively at substantially same time from the first medicine discharging unit and the second medicine discharging unit respectively under control of the control device.

3. The medical system according to claim 1,
wherein each of the first and second capsule type medical devices include a communication unit configured to perform data communication,
wherein the first and second capsule type medical devices are configured to perform data communication with each other through the respective communication unit, and wherein the first and second capsule type medical devices are configured to perform cooperative operation on the basis of the performed data communication.

4. The medical system according to claim 1,
wherein each of the first and second capsule type medical devices includes
 a medicine discharging unit, wherein a first medicine discharging unit of the first capsule type medical device is configured to control discharge of the first medicine stored in the first storage unit, and wherein a second medicine discharging unit of the second capsule type medical device is configured to control discharge of the second medicine stored in the second storage unit,
 a communication unit configured to perform data communication between the first and second capsule type medical devices, and
 a clocking unit configured to perform counting, wherein the clocking unit of the second capsule type medical device is configured to start to count in an event a notification that the first capsule type medical device has discharged the first medicine is received by the second capsule type medical device, and
 wherein the second medicine discharging unit is configured to discharge the second medicine in an event the count counted by the clocking unit of the second capsule type medical device reaches a predetermined value.

5. The medical system according to claim 1,
wherein each of the first and second capsule type medical devices includes a photographing unit configured to photograph a site in the body, and
 a lighting unit,
wherein in an event the first capsule type medical device receives, from the second capsule type medical device, a notification that the second capsule type medical device starts to photograph the site, the first capsule type medical device is configured to control lighting of the lighting unit of the first capsule type medical device.

6. The medical system according to claim 1,
wherein each of the first and second capsule type medical devices includes an extraction unit configured to extract cells inside the body, and
wherein, in an event the second capsule type medical device receives a notification of completion of cell extraction by the extraction unit of the first capsule type medical device, the second capsule type medical device is configured to start extraction of cells by use of the extraction unit of the second capsule type medical device.

7. The medical system according to claim 1,
wherein each of the first and second capsule type medical devices includes:
 a marker unit configured to give a marker to a site in the body,
 a detection unit configured to detect the marker, and
 a medicine discharging unit, wherein a first medicine discharging unit of the first capsule type medical device is configured to control discharge of the first medicine stored in the first storage unit, and wherein a second medicine discharging unit of the second capsule type medical device is configured to control discharge of the second medicine stored in the second storage unit,
wherein one of the first and second capsule type medical devices is configured to give a marker to the specific site in the body by use of the corresponding marker unit, and
wherein the other capsule type medical device of the first and second capsule type medical devices is configured to control the medicine discharging unit of the other capsule type medical device to discharge the medicine to the specific site in an event the other capsule type medical device detects the marker by use of the corresponding detection unit.

8. The medical system according to claim 1,
wherein each of the first and second capsule type medical devices includes:
 a marker unit configured to give a marker to a site in the body,
 a detection unit configured to detect the marker, and
 a photographing unit configured to photograph a site in the body,
wherein one of the first and second capsule type medical devices is configured to give a marker to the specific site in the body by use of the corresponding marker unit, and
wherein the other capsule type medical device of the first and second capsule type medical devices is configured to control photographing unit to photograph the specific site in an event the other capsule type medical device detects the marker by use of the corresponding detection unit.

* * * * *